(12) United States Patent
Reel et al.

(10) Patent No.: US 7,483,136 B2
(45) Date of Patent: Jan. 27, 2009

(54) REFRACTIVE INDEX MATCHING IN CAPILLARY ILLUMINATION

(75) Inventors: Richard T. Reel, Hayward, CA (US); Eric S. Nordman, Palo Alto, CA (US); Tomoyuki Sakai, Kokubunji (JP); Satoshi Takahashi, Hitachinaka (JP); Ryoji Inaba, Hitachinaka (JP)

(73) Assignee: Applied Biosystems Inc., Foster City, CA (US)

( * ) Notice: Subject to any disclaimer, the term of this patent is extended or adjusted under 35 U.S.C. 154(b) by 192 days.

(21) Appl. No.: 11/356,875

(22) Filed: Feb. 16, 2006

(65) Prior Publication Data

US 2007/0053186 A1   Mar. 8, 2007

Related U.S. Application Data

(60) Provisional application No. 60/653,606, filed on Feb. 16, 2005.

(51) Int. Cl.
  *G01N 21/00* (2006.01)
(52) U.S. Cl. ........................... 356/337; 356/341
(58) Field of Classification Search ......... 356/244–246, 356/337–343
  See application file for complete search history.

(56) References Cited

U.S. PATENT DOCUMENTS

| | | | | | |
|---|---|---|---|---|---|
| 3,975,084 | A | * | 8/1976 | Block | 356/335 |
| 4,577,970 | A | * | 3/1986 | Meserol | 356/440 |
| 5,037,199 | A | * | 8/1991 | Hlousek | 356/246 |
| 5,170,056 | A | * | 12/1992 | Berard et al. | 250/341.2 |
| 5,324,401 | A | * | 6/1994 | Yeung et al. | 204/452 |
| 5,484,571 | A | * | 1/1996 | Pentoney et al. | 422/82.08 |
| 5,565,978 | A | * | 10/1996 | Okubo et al. | 356/128 |
| 5,895,920 | A | | 4/1999 | Carlson | |
| 6,184,990 | B1 | | 2/2001 | Amirkhanian et al. | |
| 6,281,975 | B1 | * | 8/2001 | Munk | 356/440 |
| 6,487,349 | B2 | * | 11/2002 | Wach et al. | 385/115 |
| 6,683,314 | B2 | * | 1/2004 | Oostman et al. | 250/461.2 |
| 6,797,139 | B2 | * | 9/2004 | Bahatt et al. | 204/452 |
| 2003/0226756 | A1 | * | 12/2003 | Inaba et al. | 204/601 |

OTHER PUBLICATIONS

Optical Gels: A Light Bridge to the Future, Nye Lubricants, Inc., www.nyelubricants.com/techarticles/optpdfs/nye_optical_gels_v2.pds.

International Search Report and the Written Opinion of the International Searching Authority for Int'l application No. PCT/US06/05588 dated Jan. 4, 2008.

* cited by examiner

*Primary Examiner*—L. G Lauchman
*Assistant Examiner*—Jarreas C Underwood

(57) ABSTRACT

System and method for fluorescent light excitation and detection from samples to enhance the numerical aperture and/or reduce the cross-talk of the fluorescent light.

18 Claims, 34 Drawing Sheets

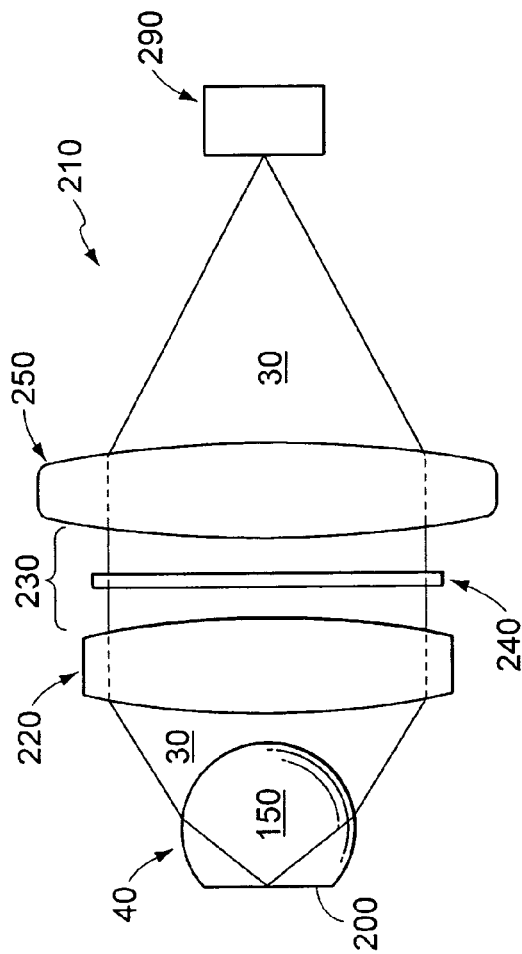
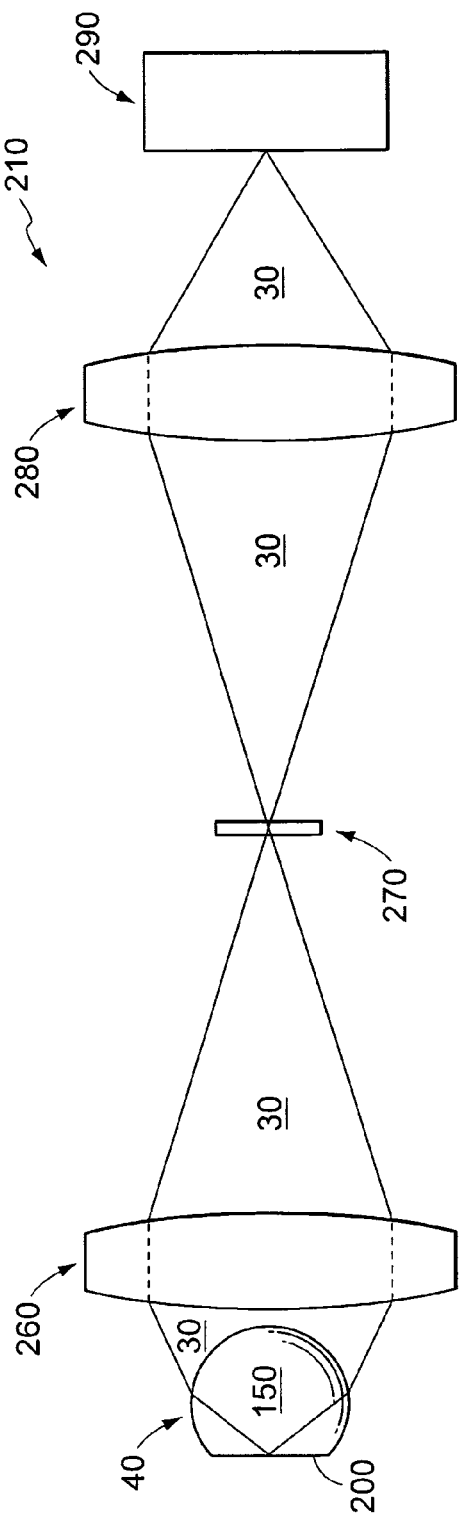
FIG. 6A
FIG. 6B

US 7,483,136 B2

REFRACTIVE INDEX MATCHING IN CAPILLARY ILLUMINATION

RELATED APPLICATION

This application claims the benefit of U.S. Provisional Application No. 60/653,606 filed Feb. 16, 2005, the disclosure of which is herein incorporated by reference in its entirety.

FIELD

The present teachings relate to devices and methods for generating and detecting fluorescence.

INTRODUCTION

Molecular biology and other sciences can utilize fluorescent detection because of its wide acceptance and sensitivity. Examples of methods utilizing fluorescent detection include chromatography and electrophoresis. Fluorescent light can be generated by exciting dyes in a sample using excitation light or chemical means. The fluorescent light emitted can be diffuse due to low concentrations of dye in the sample. It is desirable to collect more of the diffuse light to increase the efficiency of fluorescent detection.

The fluorescent light emitted can be proportional to the amount of excitation light that can be directed to the detection zone. For non-coherent light sources, such as, for example, light emitting diodes (LEDs), filament lamps, and arc lamps, only a small amount of the light can typically be directed through the wall of the sample housing to the detection zone. To provide sufficiently high irradiance of excitation light at the detection zone, lasers have been used to focus light through the wall of the sample housing. Lasers at desirable wavelengths, however, are often large, expensive, and consume a lot of power.

Due to the coherent nature of laser light, lasers have also been used to focus light into an end of a tube shaped sample housing having an inner core to illuminate the detection zone. Coupling illumination to propagate along an axis of a sample housing using non-laser excitation light, however, has not been realized because of problems coupling non-coherent light into the sample housing. For example, in the case where the housing is a capillary with an inner core, it is difficult to couple non-coherent light into the core to propagate along the axis of the capillary.

Fluorescent light detection systems can benefit from smaller, lower cost, and lower power excitation light sources. It is desirable to replace lasers with non-coherent excitation light sources that provide sufficient excitation light at the detection zone by, for example, coupling illumination to propagate down housing to the detection zone.

SUMMARY

It is to be understood that both the foregoing general description and the following description of various embodiments are exemplary and explanatory only and are not restrictive.

In various embodiments, the present teachings provide an excitation system for analyzing samples. The excitation system further comprises: a light source; a housing, wherein the housing transports samples and propagates light from the light source by total internal reflection; a coupling optical element configured to introduce light from the light source into the housing through a wall of the housing; and an index matching compound disposed in such a manner so as to optically couple the housing and the coupling optical element.

In other embodiments, the present teachings provide a method for exciting fluorescence of samples comprising: transporting a plurality of samples through a detection zone with a capillary; and directing a non-coherent light into the capillary with a coupling optical element and an index matching compound that optically couples the coupling optical element and the capillary.

In still other embodiments, the present teachings provide a system for analyzing samples comprising: a light source that provides a non-coherent excitation light; at least one housing, wherein the housing transports samples and propagates the non-coherent excitation light by total internal reflection; a coupling optical element configured to introduce the non-coherent excitation light into the at least one housing through a wall of the at least one housing; a index matching compound disposed between the at least one housing and the coupling optical element, and at least one NA enhancing optical element to collect an emitted fluorescence, wherein the NA enhancing optical element is constructed of a first material and the housing is constructed of a second material, wherein the first material has a greater index of refraction than the second material.

BRIEF DESCRIPTION OF THE DRAWINGS

The accompanying drawings, which are incorporated in and constitute a part of this specification, illustrate various embodiments. In the drawings.

FIGS. 6A-6B, 7-10 illustrate diagrammatical views of various embodiments of fluorescent light detection systems;

DESCRIPTION OF VARIOUS EMBODIMENTS

Figure 1:
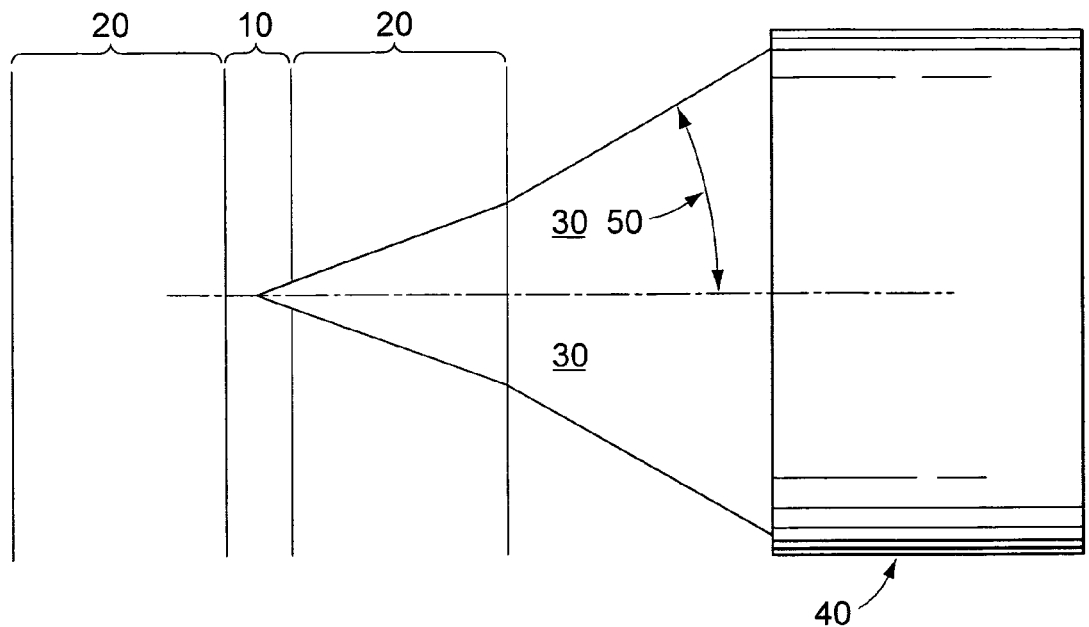
FIG. 1 illustrates a diagrammatical view of various embodiments of a sample, housing, and NA enhancing optical element.

Reference will now be made to various exemplary embodiments, examples of which are illustrated in the accompanying drawings. Wherever possible, the same reference numbers are used in the drawings and the description to refer to the same or like parts.

The term "light source" as used herein refers to a source of irradiance (can be measured in photons/mm$^2$) that can provide excitation that results in fluorescent emission. Irradiance can be related to fluorescent light in most cases because fluorescent light is proportional to the number of photons available from the light source for excitation. Light sources can include, but are not limited to, lasers, solid state laser, laser diode, diode solid state lasers (DSSL), vertical-cavity surface-emitting lasers (VCSEL), LEDs, phosphor coated LEDs, organic LEDs, inorganic-organic LEDs, LEDs using quantum dot technology, LED arrays, filament lamps, arc lamps, gas lamps, and fluorescent tubes. Light sources can have high irradiance, such as lasers, or low irradiance, such as LEDs.

The term "non-coherent light" as used herein refers to irradiance from a non-laser light source. Non-coherent light sources can include, but are not limited to LEDs, phosphor coated LEDs, organic LEDs, inorganic-organic LEDs, LEDs using quantum dot technology, LED arrays, filament lamps, arc lamps, gas lamps, and fluorescent tubes.

The term "fluorescent light" as used herein refers to a light emitted by an excited sample. Fluorescent light can be emitted in all directions. Fluorescent light can be related to detection signal because detection signal is proportional to the number of photons of fluorescent light collected from the sample. Fluorescent light can be emitted by a sample excited by excitation light, as in fluorescence, or electrically excited.

The term "coupling optical element" as used herein refers to a singlet or assembly of components in physical contact with the housing that can focus excitation light to propagate within a housing while enabling fluid connection to an end of the housing, as shown for example in FIGS. 18A-D, 21-24, 25A-C, and 26-27. A coupling optical element can include a cone, a truncated sphere, a hyperhemisphere, a spherical surface combined with a cylindrical surface, a spherical surface combined with a planar surface, a meniscus lens, etc. The components of a coupling optical element can be bonded or coupled with composition such as a solid or a fluid of suitable index that does not substantially fluoresce. In one aspect, a solid immersion optical configuration may be provided by the aforementioned composition. The index of the composition can be similar to the index of the material of the lens and/or the material of housing. In particular, the index of refraction of a fluid coupling the housing and the coupling optical element can be less than or equal to the index of refraction of the coupling optical element. According to various embodiments, the index of refraction of the fluid coupling the housing and the coupling optical element can be from about 1.43 to about the index of refraction of the coupling optical element. Coupling optical element can be constructed of BK7, PBH71, LaSFN9, or other high index glasses, plastics, such as, for example, methyl methacrylate, polycarbonate, or a combination of glass and plastic. The term "lens" as used herein can refer to a single component or singlet, such as a truncated sphere, meniscus lens, a concave lens, a convex lens, etc. or a system that can include multiple components.

The term "NA enhancing optical element" as used herein refers to a singlet assembly satisfying at least two aplanatic conditions as illustrated in FIGS. 3A-3E. The aplanatic conditions can reduce the divergence angle of a bundle of fluorescent photons emitted from any point in the sample object plane or increase the convergence of a bundle of excitation rays delivered to any point in the object plane. The cemented surfaces can have identical curvature (infinite in the case of planar surfaces). The uncemented or outside surfaces each substantially satisfy a different aplanatic condition. Exemplary NA enhancing optical elements can include a truncated sphere, a spherical surface combined with a cylindrical surface, a spherical surface combined with a planar surface, a meniscus lens, etc. The components of a NA enhancing optical element can be bonded or coupled with a fluid of suitable index that does not substantially fluoresce. The components of a NA enhancing optical element can be stationary or movable relative to each other such as a scanning system. NA enhancing optical elements can be constructed of BK7, PBH71, LaSFN9, or other high index glasses.

The term "detector" as used herein refers to any component or system of components that can detect light including a charged coupled device (CCD), back-side thinned CCD, cooled CCD, a photodiode, a photodiode array, a photo-multiplier tube (PMT), a PMT array, complimentary metal-oxide semiconductor (CMOS) sensors, CMOS arrays, a charge-injection device (CID), CID arrays, etc. The term "cycle" as used herein refers to the period of time that the detector collects light before converting it to electrical signal.

The term "housing" as used herein refers to any structure that provides containment or support to the sample. The housing can be transparent to provide entry to excitation light and exit to fluorescent light. The housing can be constructed of glass, plastic such as low fluorescence plastic, fused silica such as synthetic fused silica or synthetic quartz, etc. The housing can take any shape including one or more tubes (various types), capillaries, assemblies of capillaries, etched channel plates, molded channel plates, embossed channel plates, wells in a multi-well tray, chambers in a microcard, regions in a microslide, etc.

The term "dye" as used herein refers to any dye in any form or quantum dots in the sample. The dye can emit fluorescent light via fluorescence. Fluorescent dyes can be used to emit different colored light depending on the dyes used. Several dyes will be apparent to one skilled in the art of dye chemistry. One or more colors can be collected for each dye to provide identification of the dye or dyes detected. The dye can be based or associated with other chemical species such as proteins, carbohydrates, etc.

The term "cross-talk" as used herein refers to fluorescent light emitted from one sample appearing in the detection position of another sample. The samples can be in different housings or in the same housings. The cross-talk can be the result of reflection, scattering, and/or refraction from components in the system.

The term "translation mechanism" as used herein refers to a mechanism for moving one or more elements along at least one axis or path. The translation mechanism can move elements, such as, for example, the mask, NA enhancing optical element, and/or housings. The translation mechanism can provide controllable movement mechanically (gears, pneumatic, cams, lead screws, ball screws etc.), electrically (actuators, linear motors, etc.), piezoelectrically, and/or magnetically (induced field movement, solenoids, etc.). The control can be provided by computer or electrical circuitry designed to provide the desirable movement corresponding to the detector parameters.

The present teachings relate to apparatus and methods for exciting and/or collecting fluorescence. Turning first to collection of fluorescence, the sample can include a dye in a fluid or solid. The sample emits fluorescent light in all directions. The collection system collects a portion of this light, typically a cone of light.

According to various embodiments, as illustrated in FIG. 1, sample 10 can be bounded by housing 20. Fluorescent light 30 can be refracted to form a cone of light with a half angle 50 available for the NA enhancing optical element 40. According to Snell's Law, a change in index of refraction in the light path can refract the light and thus affect the size of the cone and therefore the quantity of light exiting the samples that can be collected by the optics. According to various embodiments, the sample 10 can have an index of refraction of about 1.29 to about 1.41, and the housings 20 can have an index of refraction of about 1.46 to about 1.6. According to various embodiments, an index matching fluid can be positioned between the housing 20 and the NA enhancing optical element 40. According to various embodiments, air or fluid can be positioned between the housing 20 and the NA enhancing optical element 40.

According to various embodiments, the depth of sample along the optical axis can be small. According to various embodiments, the distance can be 5 micrometers to 200 micrometers deep. The fluorescent light can be emitted in a narrow depth of field substantially decreasing spherical aberrations. According to various embodiments, an aplanatic condition can be provided by positioning the sample at the radius of curvature of a solid lens as described in patent application U.S. Ser. No. 09/564,790 to Richard T. Reel titled "Optical System and Method for Optically Analyzing Light from a Sample" that is herein incorporated by reference in its entirety. According to various embodiments, other aplanatic conditions are described in Kidger, Michael J., *Fundamental Optical Design* (2002), herein incorporated by reference in its entirety.

Figure 2A:
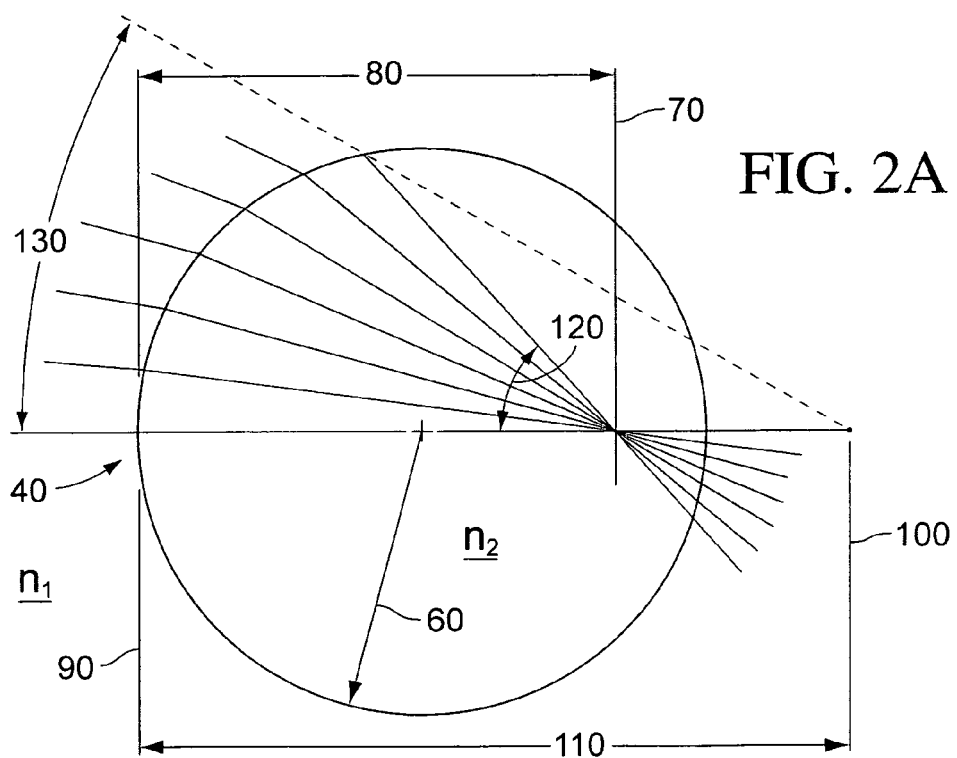
FIGS. 2A-2B illustrate cross-sectional views of various embodiments of NA enhancing optical elements.
Figure 2B:
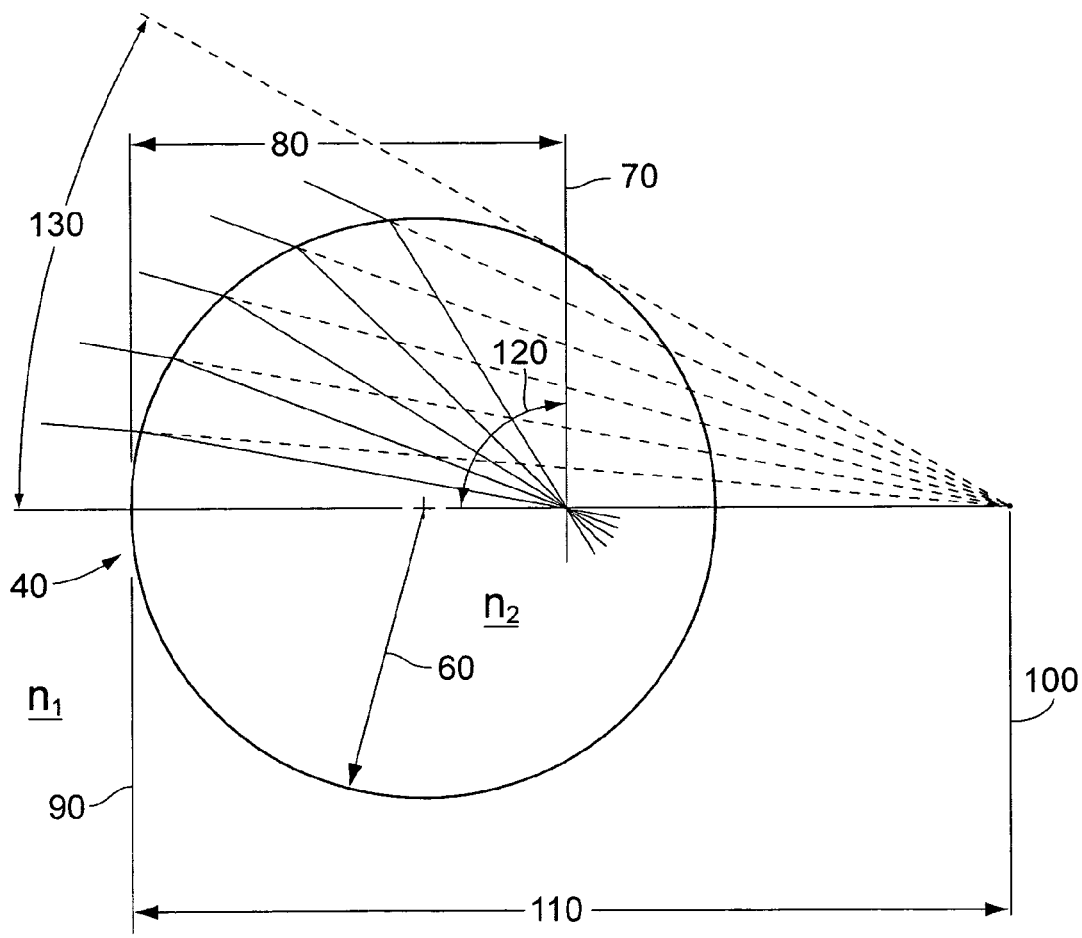

According to various embodiments, the amount of fluorescent light collected can be a function of the index of refraction ($n_2$) of the NA enhancing optical element 40 and the index of refraction ($n_1$) around the NA enhancing optical element 40. As illustrated in FIGS. 2A and 2B, NA enhancing optical element 40 can have radius (R) 60 and source plane 70 where the source plane 70 has a distance 80 from the front end 90 of NA enhancing optical element 40, where the distance 80 can be calculated as $R*(n_1+n_2)/n_2$. The NA enhancing optical element 40 can refract the fluorescent light from source plane 70 so that it appears to come from plane 100 and decrease the cone of light from half angle 120 to half angle 130 providing more collection of fluorescent light. Plane 100 has a distance 110 from the front end 90 of the NA enhancing optical element 40, where the distance 100 can be calculated as $R*(n_1+n_2)n_1$. According to various embodiments, FIG. 2B illustrates a NA enhancing optical element 40 with a higher index of refraction than the NA enhancing optical element 40 illustrated in FIG. 2A. Examples of high index of refraction materials include fused silica (n=1.46), optical glasses such as BK7 (n=1.52) and LaSFN9 (n=1.85), and plastics such as polycarbonate (n=1.56). According to various embodiments, the material used to construct can be better served by using a low fluorescing material, low Raleigh and low Raman scattering.

Figure 3A:
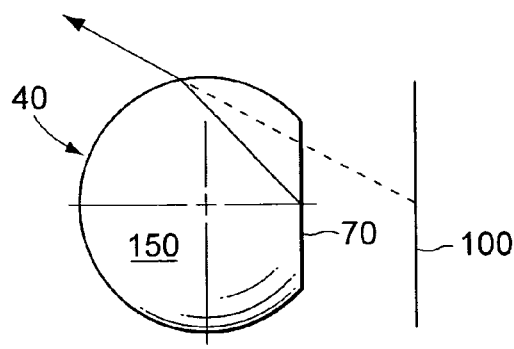
FIGS. 3A-3E and 5 illustrate cross-sectional views of various embodiments of a NA enhancing optical element.
Figure 3B:
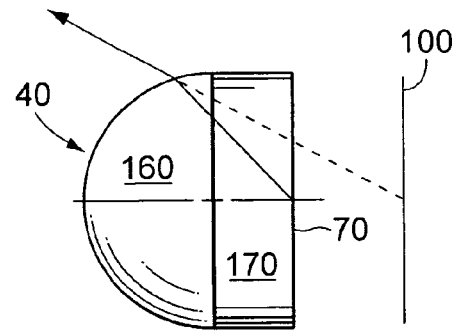
Figure 3C:
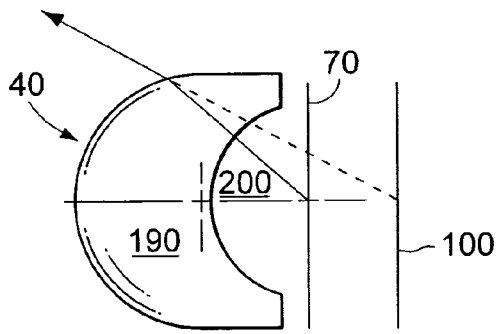
Figure 3D:
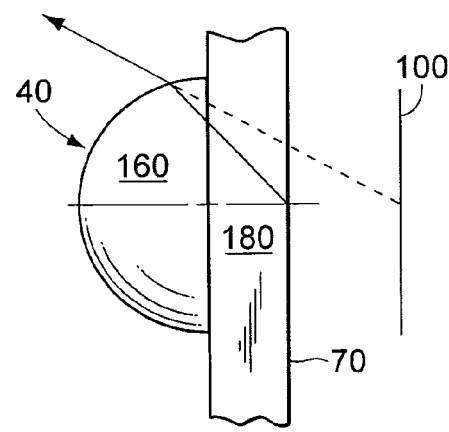
Figure 3E:
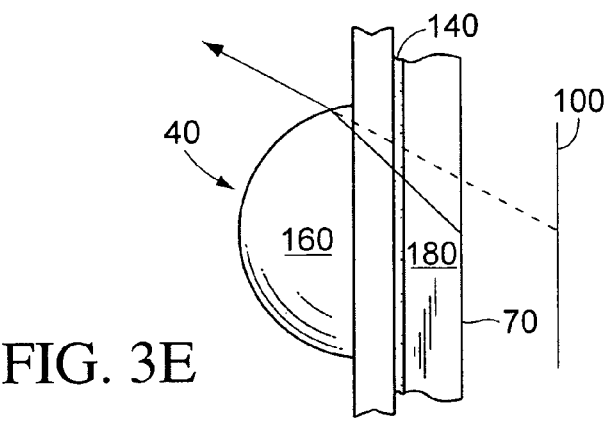

According to various embodiments, FIGS. 3A-3F illustrate different NA enhancing optical elements. FIG. 3A illustrates a NA enhancing optical element 40 including a truncated sphere 150 where the source plane 70 can be the flat portion of the truncated sphere 150. FIG. 3B illustrates a NA enhancing optical element 40 including a sphere 160 combined with a cylinder 170 where the source plane 70 can be the end of the cylinder 170. FIG. 3C illustrates a NA enhancing optical element 40 including a meniscus lens 190 where the source plane 70 can be a plane at the radius of curvature of the meniscus 200. FIG. 3D illustrates a NA enhancing optical element 40 including a sphere 160 combined with a plate 180 where the source plane 70 can be the end of the plate 180. FIG.

3E illustrates a NA enhancing optical element 40 including a sphere 160 combined with a fluid 140 and a plate 180. The sphere 160 can be bonded or coupled with the fluid 140 of similar index. The sphere 160 can be stationary or movable relative to plate 180 to provide scanning along the source plane 70.

According to various embodiments, the NA enhancing element and the housing are constructed of different material. Unlike known systems where the index of refraction of a truncated sphere and a housing are matched so that spherical aberration can be eliminated, changing the material of the NA enhancing element according to the teachings of the present invention provides a significant increase in NA enhancement with a minimal introduction of spherical aberration. Unlike known systems where an index matching fluid is added to match both truncated sphere and housings and provide a continuum minimizing the refraction of the interface of the truncated sphere and the housing, the index matching fluid matches to either the truncated sphere, the housing, or an intermediate index.

Figure 4:
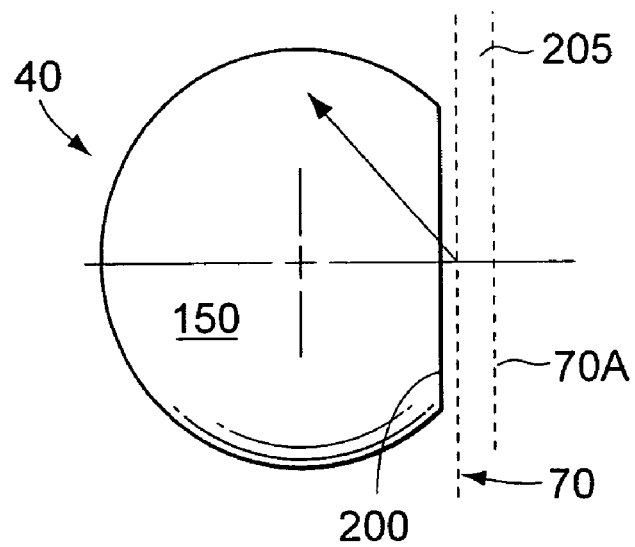
FIG. 4 illustrate the relationship of the source plane for the NA enhancing optical element and the theoretical aplanatic source plane, where
Figure 4A:
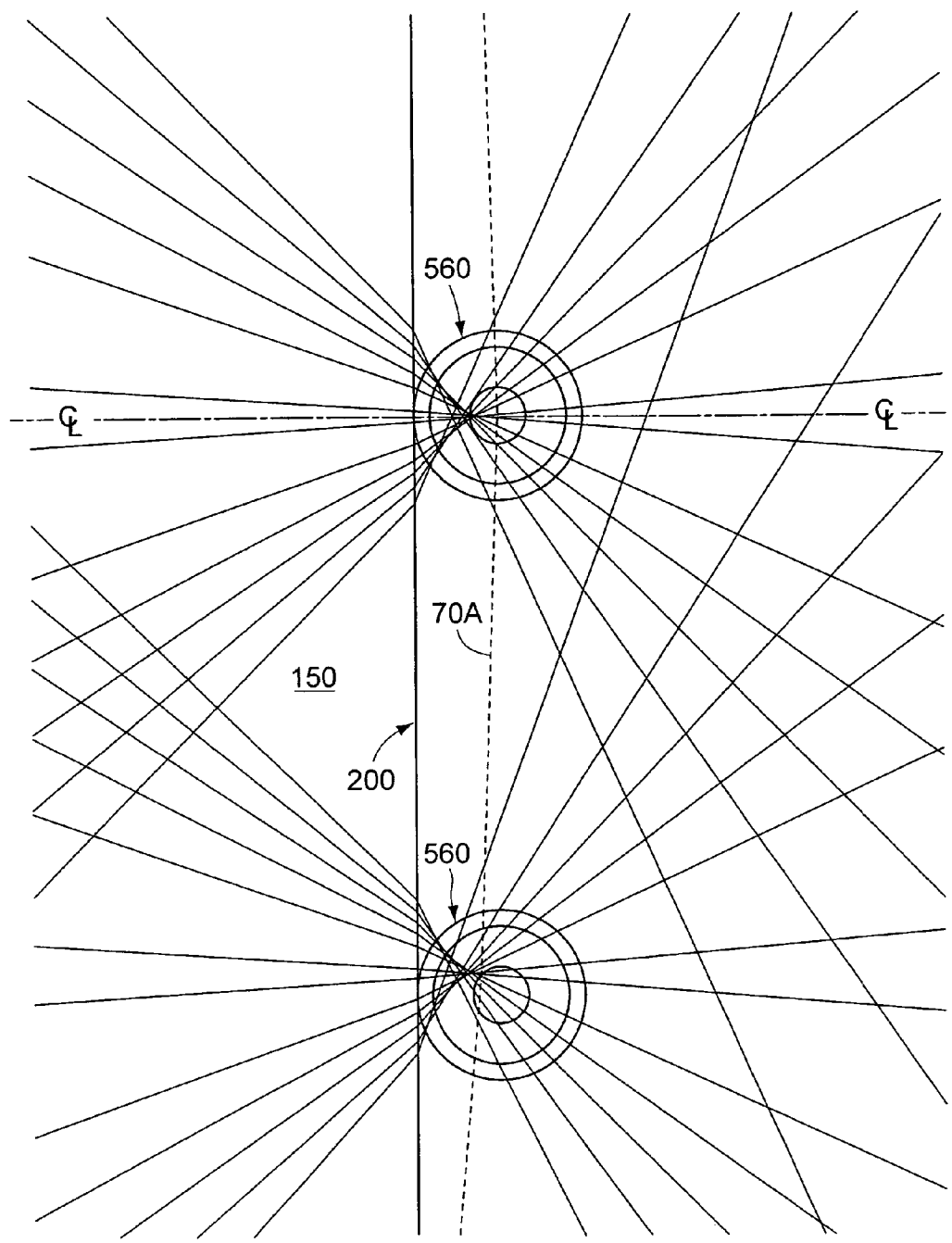
FIG. 4A illustrates the focus of light when the theoretical aplanatic source plane is used and FIG. 4B illustrates the focus of light when the source plane according to various teachings of the present invention is used.
Figure 4B:
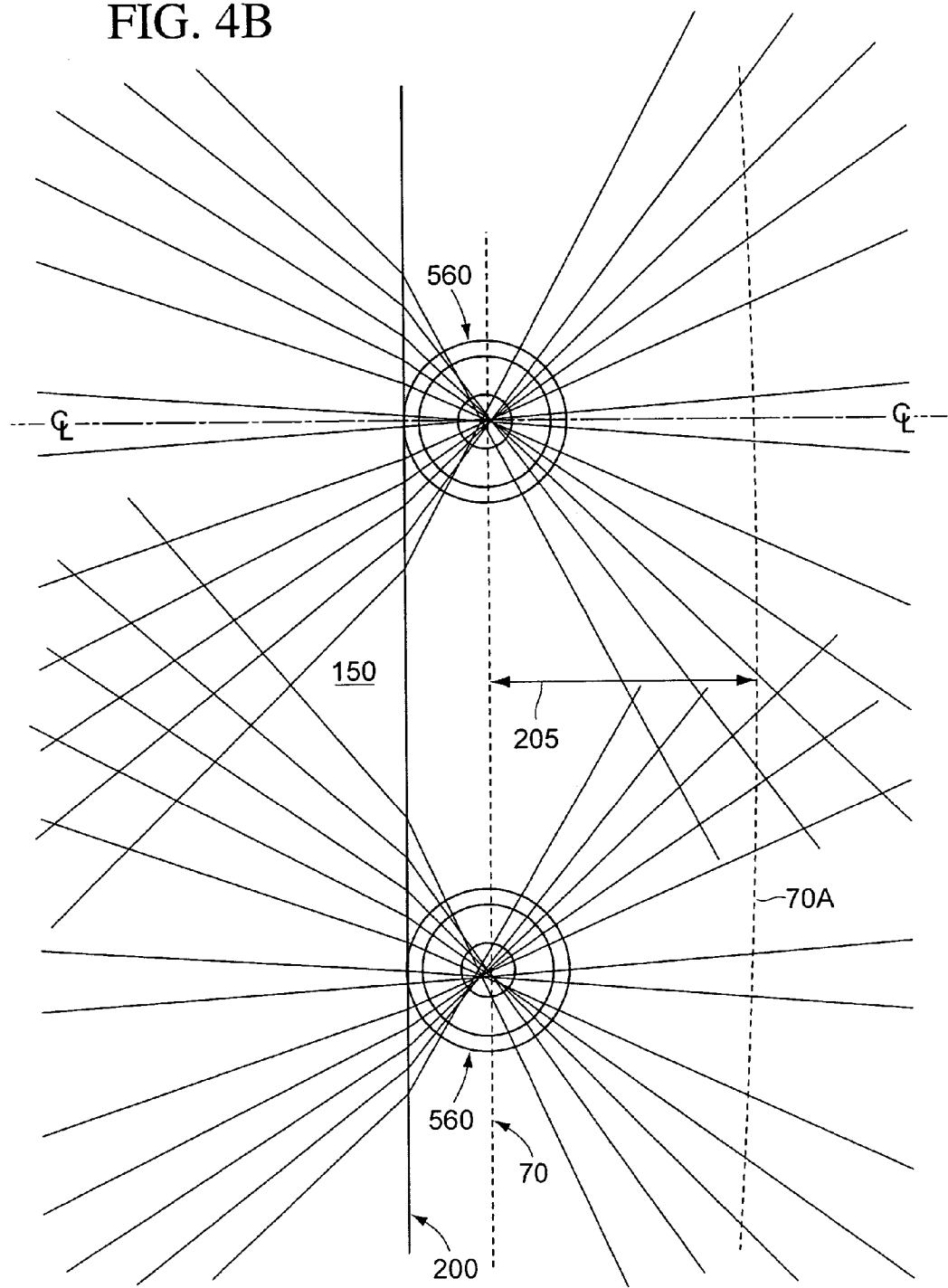

According to various embodiments, as illustrated in FIG. 4, NA enhancing optical element 40 can include truncated sphere 150 that can be truncated and/or positioned to provide an offset 205 between source plane 70 and the theoretical aplanatic source plane 70A. The offset 205 can introduce corrective aberrations to fluorescent light detection system when the truncated sphere 150 and housing 560 are constructed of different material, for example glass and fused silica. It is desirable that the index of glass be used in the truncated sphere be as high as practical. It is also desirable that the glass dispersion be as low as possible to reduce chromatic dispersion. It is further desirable that the glass dispersion be as low as possible to reduce chromatic aberration. In a confocal configuration, where the NA enhancing optical element is used for excitation or collection, the improvement approximately proportional to $n^4$ each or $n^8$ for both excitation and collection. FIG. 4A illustrates truncating the sphere 150 and positioning the housings 560 at the theoretical aplanatic source plane 70A when the sphere 150 and the housings 560 are constructed of different material. The focus is shifted from the desirable position at the center of the housing 560. FIG. 4B illustrates truncating the sphere 150 and positioning the housings 560 at the source plane 70 that is offset 205 from the theoretical aplanatic source plane 70A. The offset 205 shift that focus to the desirable center of the housing 560 to compensate for the difference in index of refraction of the truncated sphere 150 and the housing 560.

Figure 5:
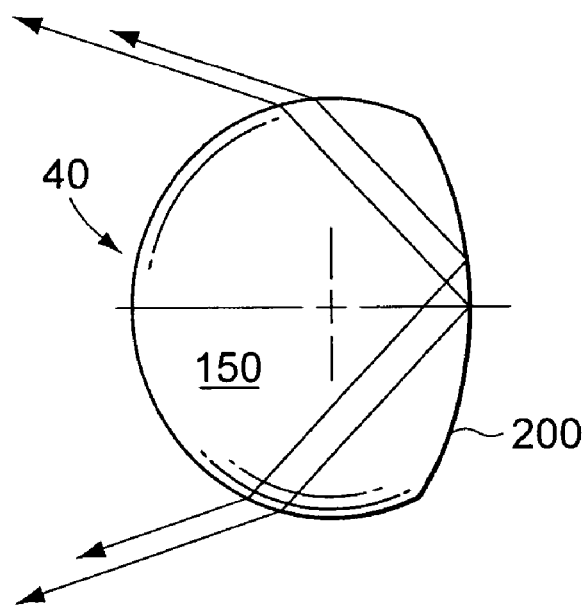

According to various embodiments, as illustrated in FIG. 5, NA enhancing optical element 40 can include truncated sphere 150 where the back end 200 is curved to provide assistance in improving imaging across a curved field of view. According to various embodiments, additional optical elements can be added to the NA enhancing optical element 40 illustrated in FIG. 5 to provide flattening of a curved field of view.

According to various embodiments, as illustrated in FIG. 6A, fluorescence light detection system 210 includes NA enhancing optical element 40 including truncated sphere 150 with offset source plane 70, lens 220, filter 240, lens 250, and detector 290. Lens 220 can form a substantially collimated region 230 with fluorescent light 30 where filter 240 can be positioned to accept desired wavelengths of the fluorescent light 30 and reject other wavelengths. Filter 240 can be an interference filter. Lens 250 can focus the fluorescent light 30 onto detector 290. According to various embodiments, FIG. 6B illustrates a fluorescent light detection system 210 similar to that illustrated in FIG. 6A except lens 260 focuses the fluorescent light 30 on filter 270 that accepts desired wavelengths of the fluorescent light 30 and rejects other wavelengths. Lens 280 focuses the fluorescent light 30 onto detector 290. Filter 270 can be positioned on a filter wheel, linear actuator, or other mechanism for switching between multiple filters.

According to various embodiments, a fluorescent light detection system can include components to spectrally separate the wavelengths of fluorescent light to provide multicolor detection including but not limited to transmission gratings, reflective gratings, prisms, grisms, software controllable filters (width and position in spectral axis) etc. According to various embodiments, the sample container or the fluorescent light detection system can be translated to decrease motion-induced blurring on the detector. According to various embodiments, a fluorescent light detection system can include folding mirrors to decrease the size of the system.

Figure 7:
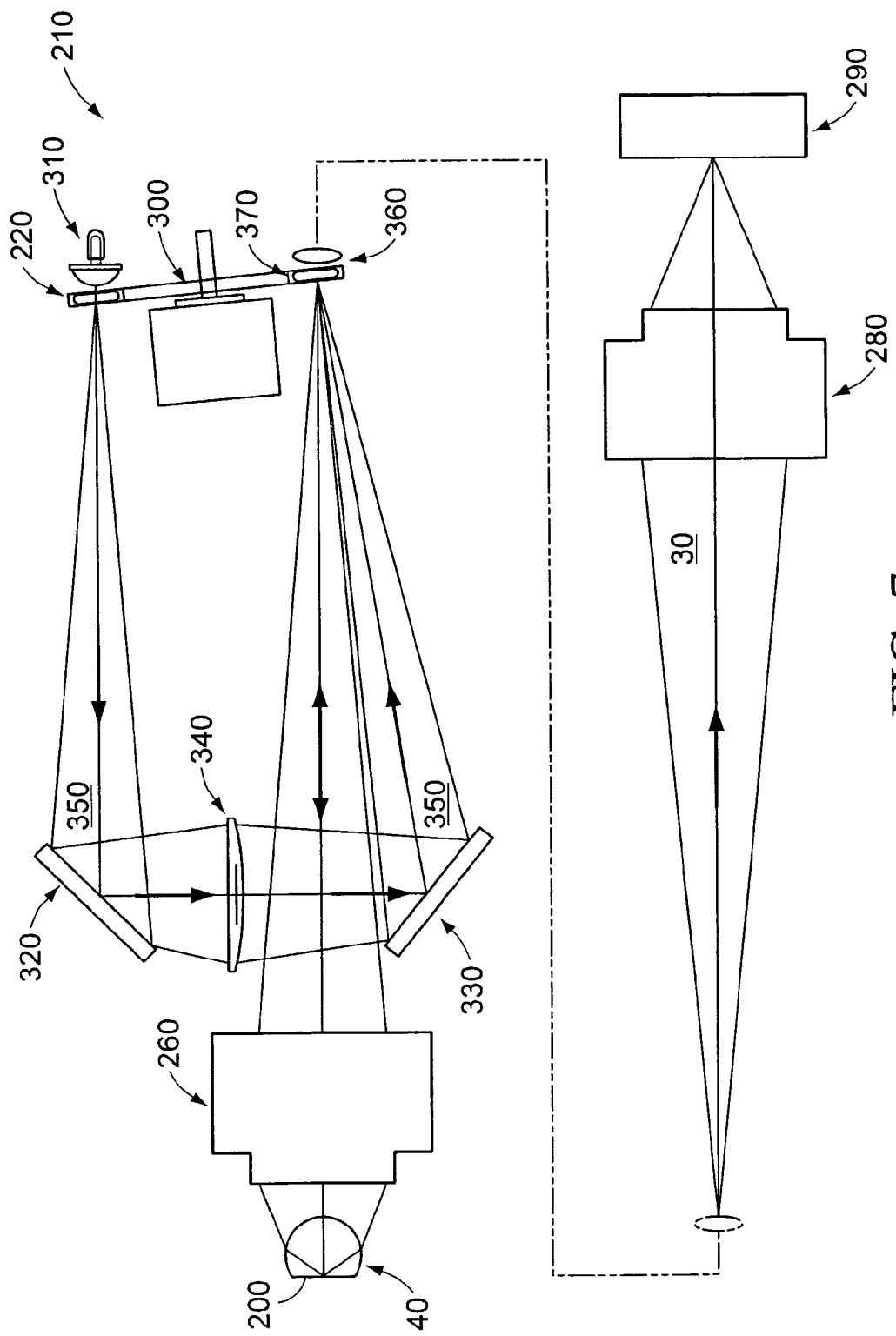

According to various embodiments, as illustrated in FIG. 7, fluorescent light detection system 210 can include light source 310, filter wheel 300 including filter 220 and filter 370, mirrors 320 and 330, lenses 340, 260, 360, and 280, NA enhancing optical element 40 including source plane 70, and detector 290. Excitation light 350 can be provided by light source 310. Excitation light can be filtered by filter 220 on filter wheel 300. Excitation light 350 can be directed to filter 370, such as a dichroic filter, on filter wheel 300 by mirrors 320 and 330 and lens 340. The filter 370 reflects excitation light 350 towards lens 260, NA enhancing optical element 40, and a sample at source plane 70. The large collection angle of NA enhancing optical element 40 can provide an increased amount of light from light source 310 to a small detection spot of the sample. The excitation light 350 can be absorbed by the sample or dyes in the sample that can emit fluorescent light 30. Fluorescent light 30 can be collected by NA enhancing optical element 40 and directed to lens 260 and filter 370. The color of fluorescent light 30 can pass through filter 370 to lens 360 and lens 280 that focus the fluorescent light 30 onto detector 290. The image can be magnified to reduce the collection angle to one that is suitable for the detector 290. According to various embodiments, lens 500 can be larger in diameter than lens 430 to avoid vignetting by making the angle of incidence for the reflection of the dichroic mirror 480 be less than 45 degrees to improve transmission, reflection, and spectral properties.

Figure 8:
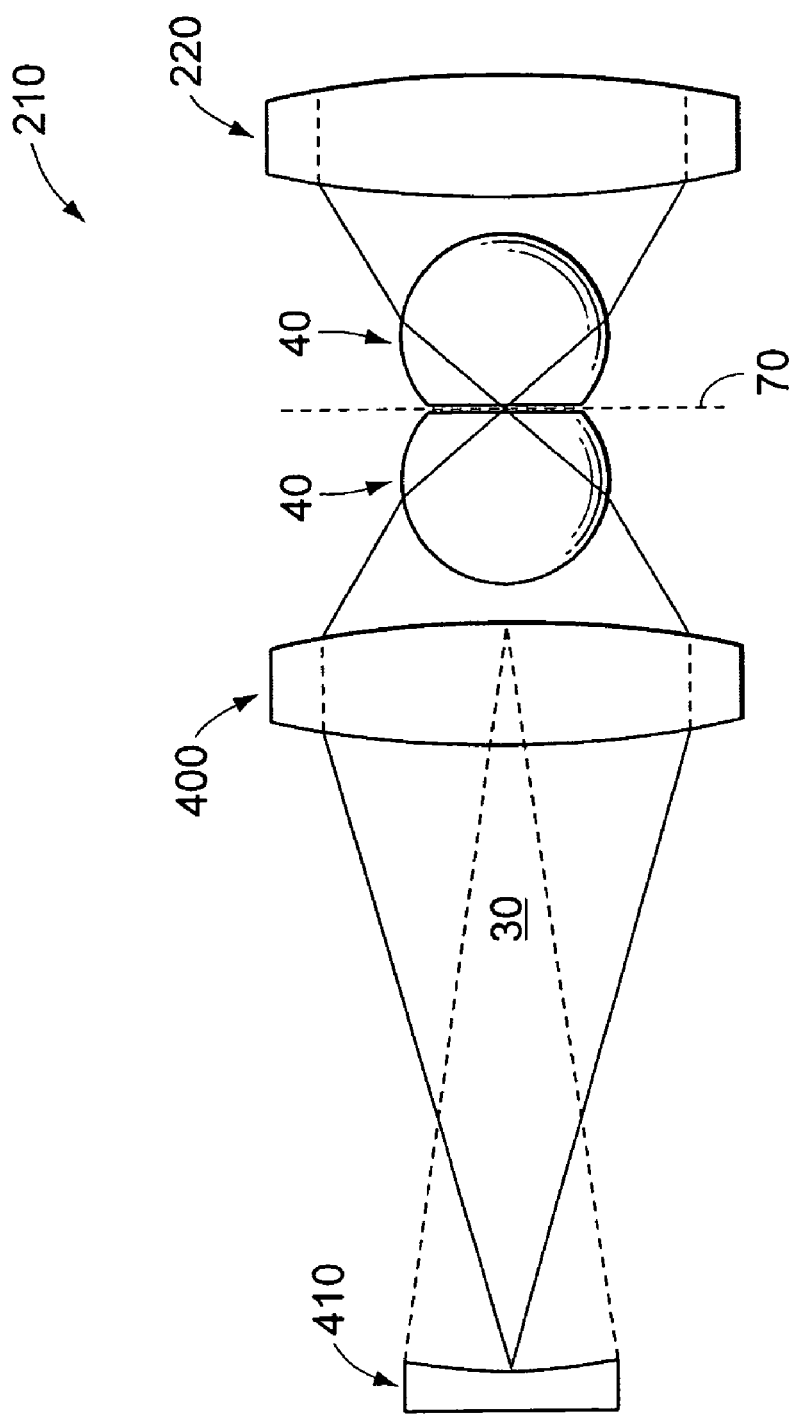
Figure 9:
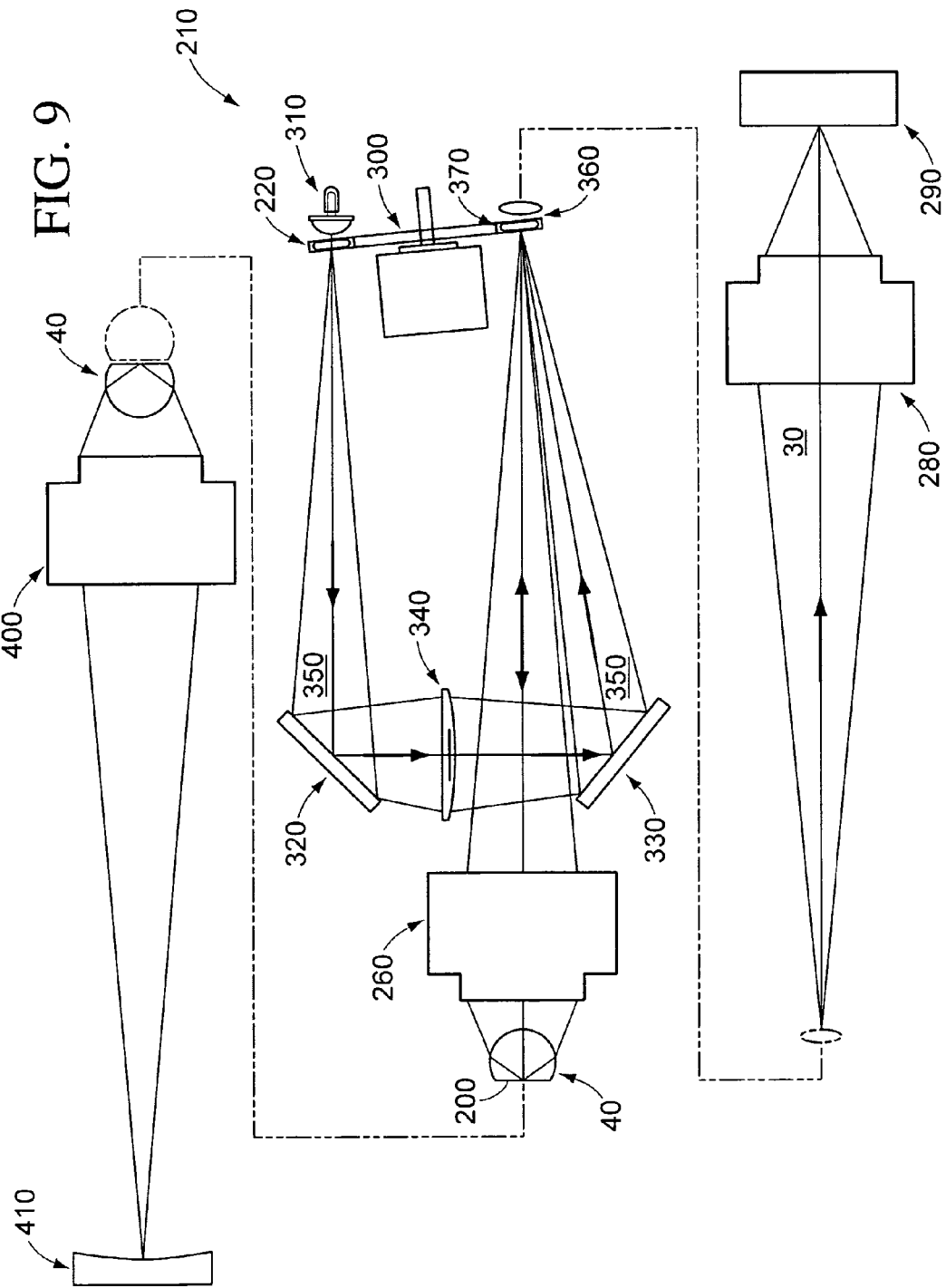

According to various embodiments, as illustrated in FIG. 8, fluorescent light detection system 210 can include two NA enhancing optical elements 40 to collect fluorescent light from both sides of the sample. The fluorescent light 30 on the opposite side of detector 290 can be collected and directed back towards detector 290 through lens 400 and mirror 410, such as a concave mirror. The fluorescent light 30 reflected from mirror 410 can be directed back through both NA enhancing optical elements 40 (co-imaged across source plane 70), lenses 220 and 250, and filter 240 toward detector 290. Collecting light from both sides of the sample can double the amount of excitation light as well as doubling the amount of fluorescent light 30 directed toward the detector 290 resulting in a 4× improvement. According to various embodiments, FIG. 9 illustrates a fluorescent light detection system 210 similar to the one illustrated in FIG. 7 with two NA enhancing optical elements 40 and a mirror 410 as illustrated in FIG. 8.

According to various embodiments, a fluorescent light detection system can include a mask providing an aperture to reduce cross-talk between multiple samples. According to various embodiments, the mask can be positioned to provide excitation and collection of fluorescent light from a single sample. According to various embodiments, samples can be positioned so that the mask provides excitation light to and collection of fluorescent light from a single sample. According to various embodiments, the mask can be positioned to provide excitation and collection of fluorescent light from a subset of samples. According to various embodiments, samples can be positioned so that the mask provides excitation and collection of fluorescent light from a subset of samples. According to various embodiments, a fluorescent light detection system can be positioned to collect fluorescent light from each sample on different portions of the detector thereby collecting individually while detecting collectively.

Figure 10:
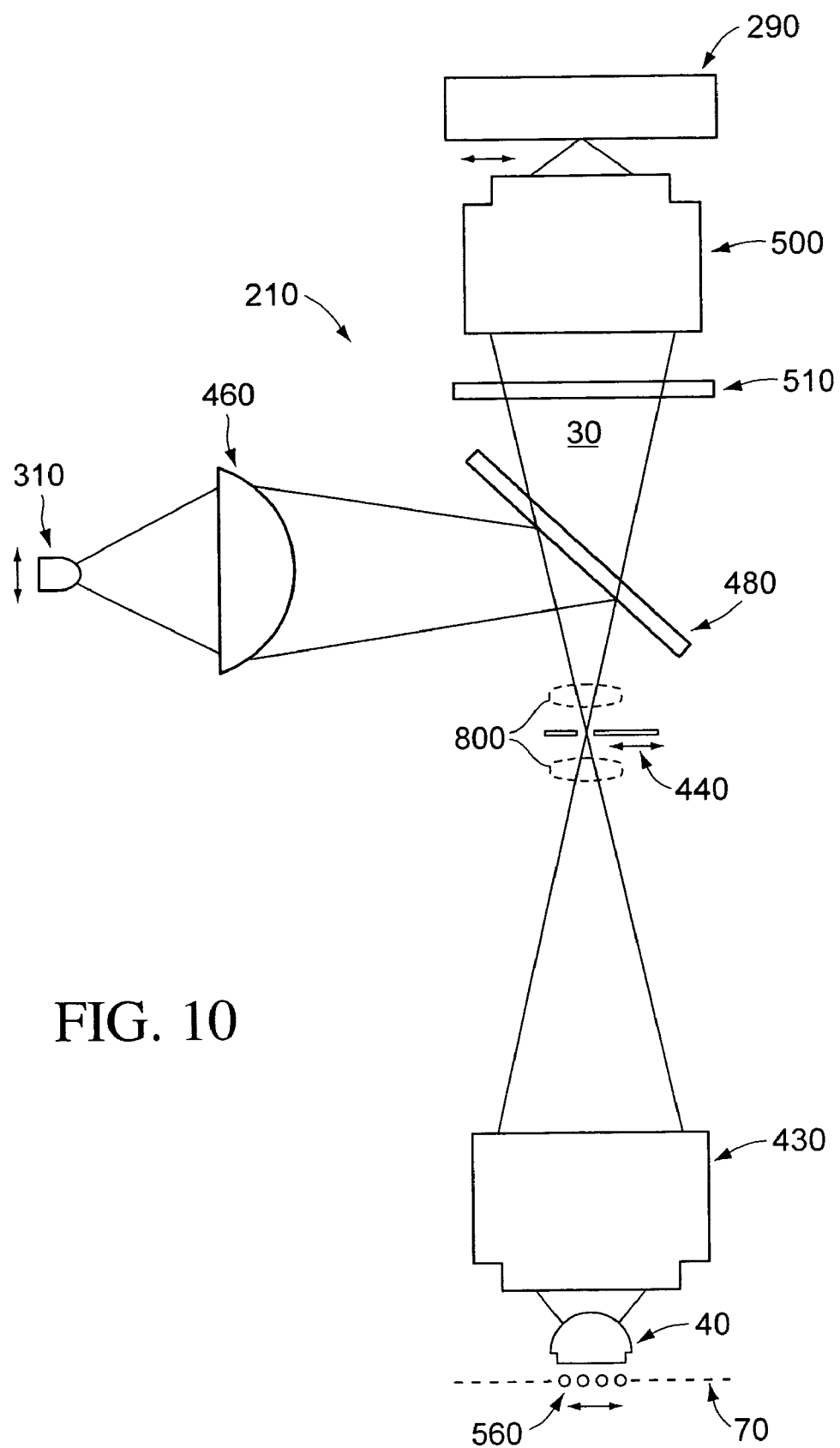

According to various embodiments, as illustrated in FIG. 10, fluorescent light detection system 210 can include sample housings 560, NA enhancing optical element 40, lenses 430, 460, 520, 500 and 800, dichroic beam-splitter 480, light source 310, mask 440, grating 510 and detector 290. According to various embodiments, mask 440 can be positioned to reduce cross-talk between multiple samples, as illustrated by the double arrow near the mask. Lenses 800, which can be positioned on either side of the mask as indicated by the broken lines, can focus light on mask 440 while remaining stationary. According to various embodiments, light source 310 can be positioned in coordination with positioning mask 440, as illustrated by the double arrow near the light source. The light source can be narrow on the order of only one aperture in the mask. Hence, the light source can be positioned from aperture to aperture in a mask by scanning with more than one aperture. According to various embodiments, sample housings 560 and/or NA enhancing optical element 40 can be positioned to reduce cross-talk between multiple samples, as illustrated by the double arrow near the sample housings. According to various embodiments, lens 500 and/or detector 290 can be positioned to reduce cross-talk between multiple samples, as illustrated by the double arrow between the lens and detector. According to various embodiments, a mirror can be positioned to direct where the image falls on the detector. According to various embodiments, the detector can be masked to control where the image falls on the detector.

Figure 11A:
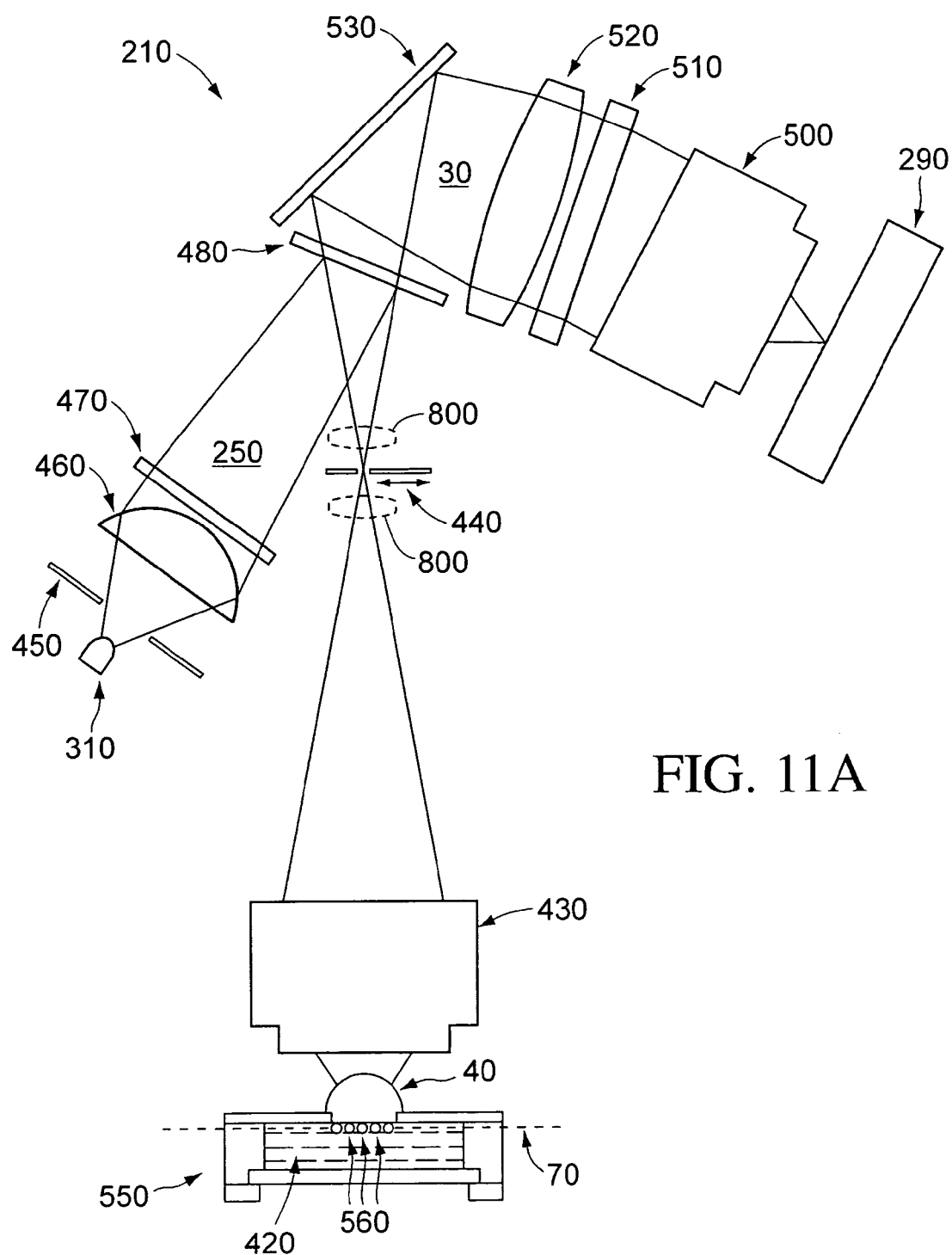
FIG. 11A illustrates a diagrammatical view of various embodiments of a light detection system.

According to various embodiments, as illustrated in FIG. 11A, fluorescent light detection system 210 can include assembly 550 that can include sample housings 560 in index matching fluid 420, NA enhancing optical element 40, lenses 430, 500, 520, 460, and 800, dichroic beam-splitter 480, filter 470, mirror 530, grating 510 and mask 440. The light source 310 can provide excitation light 250 to lens 460 that can collect the excitation light 250 from the source. Excitation light 250 can be directed to filter 470 that can condition the excitation light 250 by accepting desirable wavelengths of excitation light 250 while blocking other wavelengths. For example, filter 470 can be a bandpass filter that accepts wavelengths that excite a dye in the sample and block wavelengths that correspond to the wavelengths of the fluorescent light emitted by the dyes. Excitation light 250 can be reflected by dichroic mirror 480 to pass through an aperture in mask 440. Mask 440 can be positioned at an image plane of lens 430. The mask 440 can translate along the image plane as illustrated by the double arrow. Lenses 800 can focus light on mask 440 while remaining stationary. Excitation light 250 can be directed to NA enhancing optical element 40 and focused onto housings 560 that can be positioned in source plane 70. Excitation light 250 can be absorbed by dyes in the samples in housings 560, stimulating the dyes to emit fluorescent light 30 in all directions. NA enhancing optical element 40 can collect fluorescent light 30 and direct it to lens 430 and mask 440. The aperture in mask 440 can bound excitation light 250 and fluorescent light 30 to one housing 560 thereby reducing cross-talk between fluorescent light emitted from other housings 560. Fluorescent light 30 can pass through dichroic mirror 480, while non-fluorescent light can be rejected. Fluorescent light 30 can be reflected by mirror 530, substantially collimated by lens 520, dispersed by transmission grating 510, and focused by lens 500 onto detector 290.

Figure 11B:
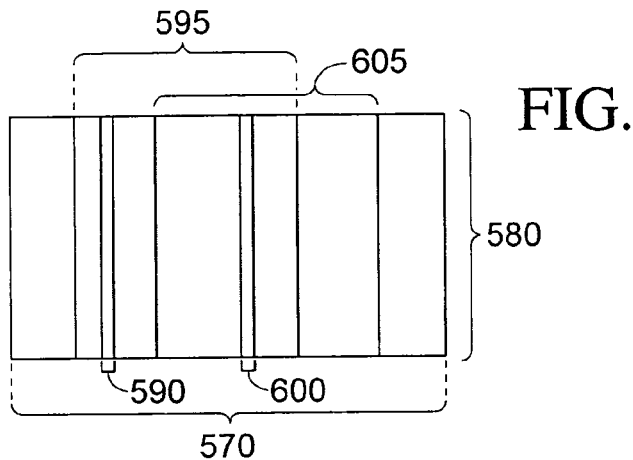
FIG. 11B illustrates a diagrammatical view of various embodiments of a portion of a detector as illustrated in FIG. 11A.

According to various embodiments, FIG. 11B illustrates a magnified view of portion 540 of detector 290 illustrated in FIG. 11A. Portion 540 has a spectral axis 570 and a spatial axis 580. Fluorescent light 30 from a single housing 560 can be dispersed across band 595 of the detector. Regions of the detector, for example 590 and 600 collect different wavelengths of light and can be measured to determine the spectral composition of the fluorescent light. Light from other housings 560 dispersed across band 605 can be displaced on the detector so different regions can be selected. The overlap of bands 595 and 605 can be reduced by clearing the detector after light from each housing is read. According to various embodiments, the region 590 can be 520 nanometers and region 600 can be 700 nanometers. According to various embodiments, fluorescent light can be collected from the detection zone while bands of dye move through the housing. According to various embodiments, blurring induced by the motion of bands of dye can be reduced by shifting the packets of charges on the detector at the same velocity as the image of the moving bands of dye on the detector. The velocity of the bands of dye passing the detection zone can be predicted because the bands of dye move at a predictable rate through the housing. The velocity of the bands of dye in the detection zone can be calculated by dividing the known separation distance by the measured separation time. According to various embodiments, the packets of charges on the detector can be accumulated by time-delay integration as described in U.S. Ser. No. 10/205,028 to Nordman et al. titled "Time-Delay Integration in Electrophoretic Detection Systems" that is herein incorporated by reference in its entirety. According to various embodiments, the mask can be positioned to excite and/or detect a different housing and/or subset of housings. According to various embodiments, the fluorescent light detection system can cycle through all the housings and/or subsets of housings such that the bands of dye detected at the beginning of the cycle have traveled no more than the full length of the detection zone during a cycle. Each cycle can capture a portion of the electropherogram from each housing. The spatial axis of the image of fluorescent bands can be converted from distance to time to create a conventional electropherogram. According to various embodiments, the number of housings that can fit on the source plane for the collector lens can determine the desirable cycling times/rate.

Figure 12A:
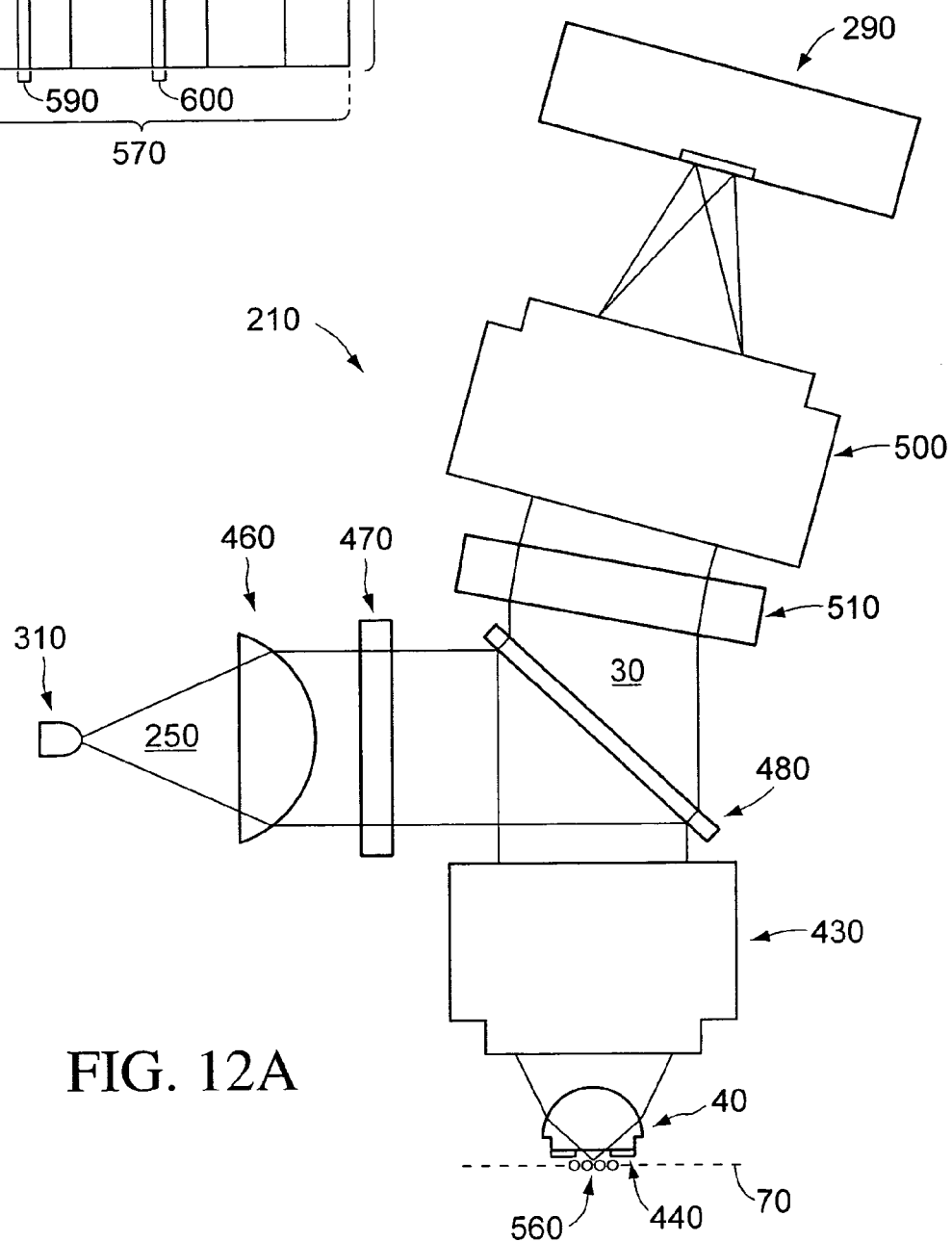
FIG. 12A illustrates a diagrammatical view of various embodiments of a light detection system.

According to various embodiments, as illustrated in FIG. 12A, fluorescent light detection system 210 can include light source 310, lenses 460, 430, and 500, NA enhancing optical element 40, filter 470, grating 510, dichroic mirror 480, detector 290, housings 560, and mask 440. The light source 310 can provide excitation light 250 to lens 460 that can collect the excitation light 250 from the source. Excitation light 250 can be directed to filter 470 that can condition the excitation light 250 by accepting desirable wavelengths of excitation light 250 while blocking other wavelengths. For example, filter 470 can be a bandpass filter that accepts wavelengths that excite a dye in the sample and block wavelengths that correspond to the wavelengths of the fluorescent light emitted by the dyes. Excitation light 250 can be reflected by dichroic mirror 480 and directed to NA enhancing optical element 40 by lens 430 to be focused onto housings 560 through mask 440, where the housings 560 can be positioned in source plane 70 offset from NA enhancing optical element 40. Excitation light 250 can be absorbed by dyes in the samples in housings 560, stimulating the dyes to emit fluorescent light 30 in all directions.

Figure 12B:
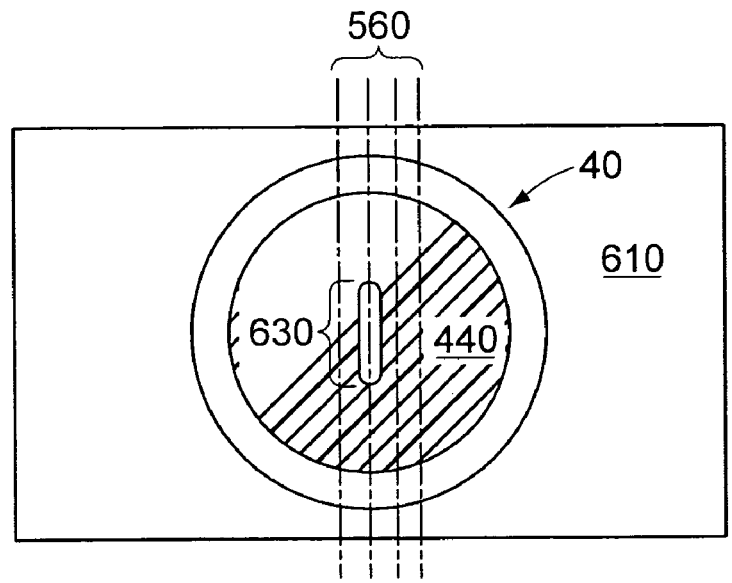
FIG. 12B illustrates a cross-sectional top view of a portion of various embodiments of a light detection system as illustrated in FIG. 12A.
Figure 12C:
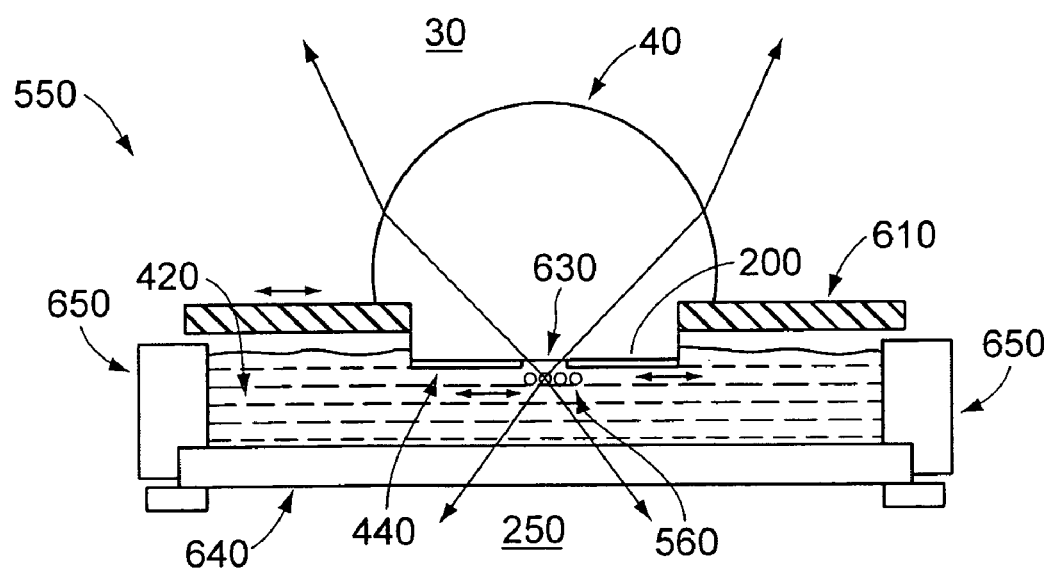
FIG. 12C illustrates a cross-sectional side view of a portion of various embodiments of a light detection system as illustrated in FIG. 12A.

According to various embodiments, the fluorescent light detection system illustrated in FIG. 12A can include a mechanism to translate housings 560 in the source plane 70 so that mask 440 can align with one housing or a subset of the housings. This translation is illustrated in FIG. 12C as a double-headed arrow near housing 560. According to various embodiments, as illustrated in FIG. 12B, mask 440 can be coupled to the back end 200 of NA enhancing optical element 40 so that the aperture in mask 440 provides detection zone 630. NA enhancing optical element 40 can collect fluorescent light 30 from the detection zone 630 and direct it to lens 430. The detection zone 630 in mask 440 can bound excitation light 250 and fluorescent light 30 to one housing or subset of housings thereby reducing cross-talk between fluorescent light emitted from other housings 560. Fluorescent light 30 can pass through dichroic mirror 480, while non-fluorescent light can be rejected. Fluorescent light 30 can be dispersed by transmission grating 510, and focused by lens 500 onto detector 290.

According to various embodiments, as illustrated in FIG. 12C, the housings 560 can be positioned in assembly 550 so that the housings 560 are immersed in index matching fluid 420. Assembly 550 can include NA enhancing optical element holder 610 and base 650. Mask 440 can be coupled to back end 200 of NA enhancing optical element 40 so that the aperture in mask 440 provides detection zone 630. Mask 440 can be a coating applied to the back end 200 of NA enhancing optical element 40. According to various embodiments, the base 650 can be translated to position housings 560 and index matching fluid 420 so that mask 440 can provide detection zone 630 to the desired position to collect fluorescent light from one housing or a subset of housings. According to various embodiments, the housings 560 can be positioned in sequence to align with the detection zone 630. According to various embodiments, base 650 can include baffling 640. Baffling 640 can form the bottom of assembly 550. According to various embodiments, baffling 640 can include an anti-reflective window to permit the excitation light 250 and/or fluorescent light 30 to exit assembly 550 on the opposite side of NA enhancing optical element 40. For example, the window can be constructed of fused silica coated with an AR material to minimize background light. According to various embodiments, baffling 640 can include a mirror to reflect fluorescent light 30 and increase the amount of fluorescent light 30 transmitted through NA enhancing optical element 40. According to various embodiments, the mirror can be a spherical surface as illustrated in FIGS. 8 and 9.

Figure 12D:
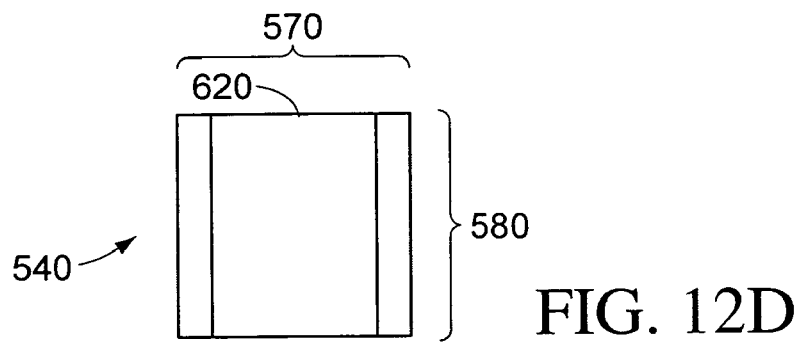
FIGS. 12D-E illustrate diagrammatical views of various embodiments of a portion of a detector as illustrated in FIG. 12A.

According to various embodiments, FIG. 12D illustrates a magnified view of portion 540 of detector 290 illustrated in FIG. 12A. Portion 540 has a spectral axis 570 and a spatial axis 580. Fluorescent light 30 from a single housing 560 can be spectrally separated into different wavelengths, for example band 620. According to various embodiments, overlapping bands can be prevented by collecting fluorescent light 30 from each housing 560 before switching to next housing 560. The integration time to collect light from each housing 560 can limit the number of housings 560. According to various embodiments, band 620 can range from 520 nanometers and 700 nanometers. According to various embodiments, the number of housings that can be positioned by the base can be determined by at least one of the base translation time, detector collection time, size of detection zone, and sample rate. According to various embodiments, sample rate can include rate at which sample travels through housing and/or rate of electrophoresis.

Figure 12E:
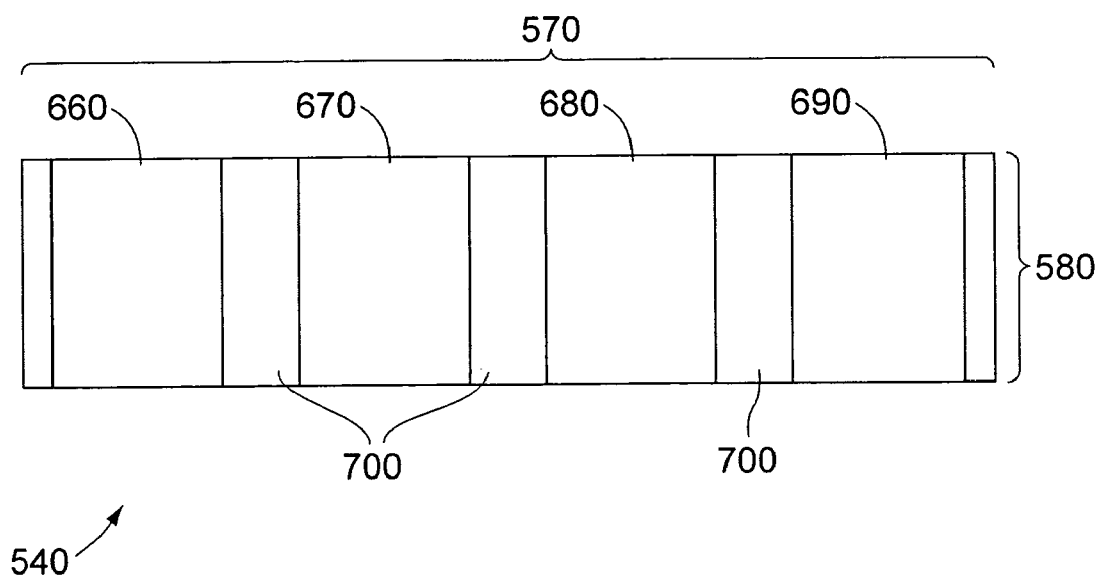

According to various embodiments, the fluorescent light detection system illustrated in FIG. 12A can include a translation mechanism to move NA enhancing optical element 40. This translation is illustrated by the double-headed arrow near holder 610. According to various embodiments, as illustrated in FIGS. 12B and 12C and described herein, NA enhancing optical element 40, mask 440, and assembly 550 can be similar to a system that includes a translation mechanism to move the housings 560. Detection zone 630 can be positioned by the translation mechanism to move the NA enhancing optical element 40. According to various embodiments, FIG. 12E illustrates a magnified view of portion 540 of detector 290 illustrated in FIG. 12A. Portion 540 has a spectral axis 570 and a spatial axis 580. Fluorescent light 30 can be detected at different wavelengths from each housing 560, for example bands 660, 670, 680, and 690, each from a different housing 560. According to various embodiments, each band 660, 670, 680, and 690 can range from 520 nanometers and 700 nanometers. According to various embodiments, the pitch or spacing of the housings 560 can be provided such that bands of adjacent housings 560 do not overlap, as illustrated in FIG. 12E. The wavelength bands for each housing 560 can be detected on the detector 290 at one interval without having to be detected separately. According to various embodiments, the detector can accumulate packets of charges by time-delay integration. The detector collection time can be matched to the sample rate.

According to various embodiments, gaps 700 can provide a range of wavelengths to permit bandpass filter 470 to exclude sufficient wavelengths to reduce overlap between bands 660, 670, 680, and 690 on portion 540 of detector 290. According to various embodiments, pitch, P, can be calculated: $P=S*R/M$, wherein S is the number of pixels on detector 290 to capture one of bands and a gap, R is the width per pixel, and M is the magnification. According to various embodiments, the size of the detector 290 can determine the number of housings 560 detected at the same time.

Figure 13:
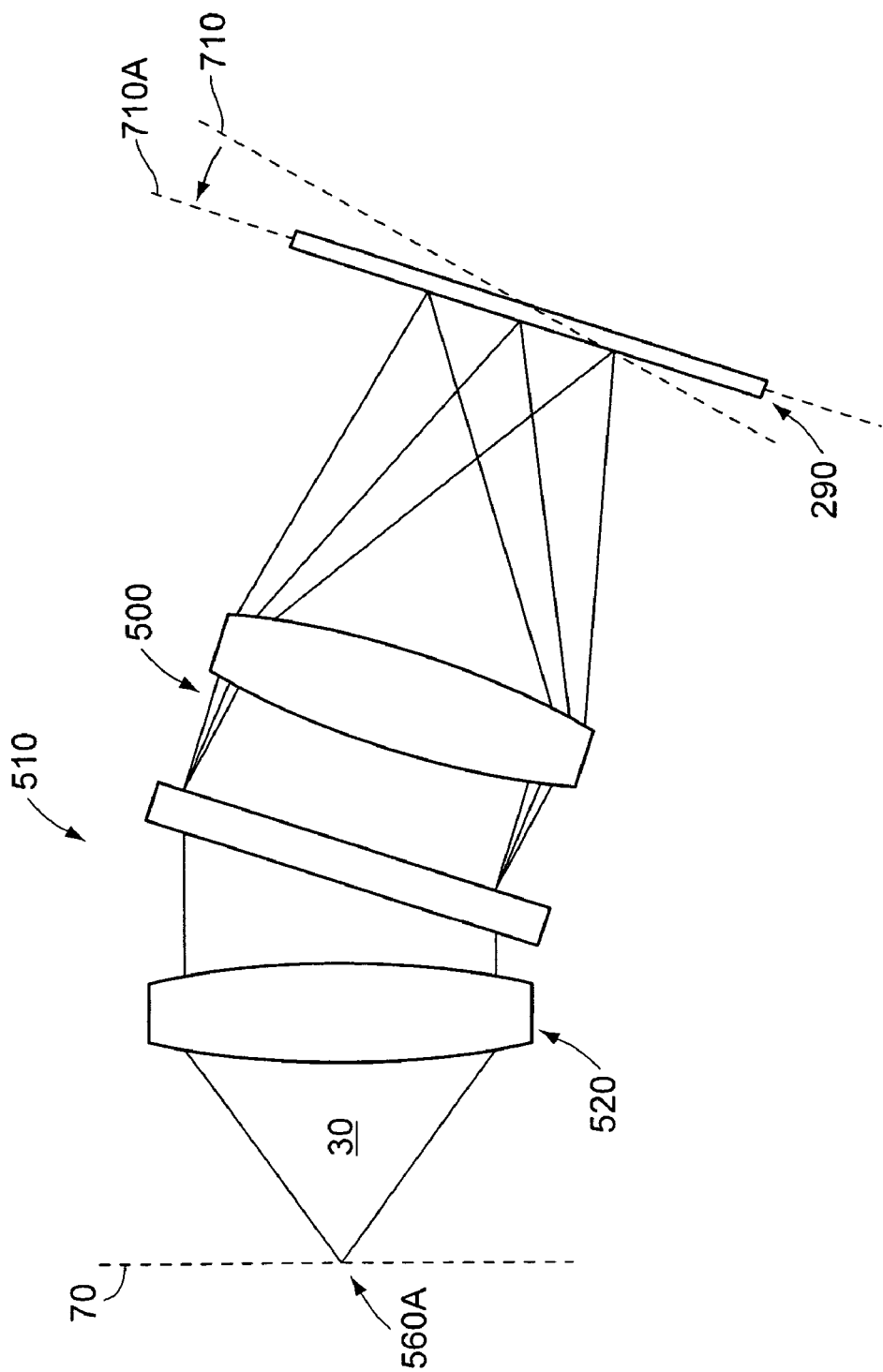
FIG. 13 illustrates a diagrammatical view of various embodiments of a light detection system.

According to various embodiments, as illustrate in FIG. 13, chromatic aberrations can be reduced by tilting the detector 290 and positioning housings 560 such that source plane 70 tilts. For example, tilting source plane 70 to position 70A as illustrated by the arrow and tilting the plane 710 of detector 290 to position 710A provides detection of fluorescent light 30 collected from housing 560A to be detected by wavelength band 720A and fluorescent light 30 collected from housing 560B to be detected by wavelength band 720B. According to various embodiments, a fluorescent light detection system including the tilting illustrated in FIG. 13, can reduce chromatic aberrations by distancing different colors.

According to various embodiments, the fluorescent light detection system illustrated in FIG. 12A can include a mechanism to translate mask 440. This translation is illustrated by the double-headed arrow near mask 440 in FIG. 12C. According to various embodiments, as illustrated in FIGS. 12B and 12C and described herein, NA enhancing optical element 40, mask 440, and assembly 550 can be similar to system that includes a translation mechanism to move the housings 560 except that the mask 440 is not coupled to NA enhancing optical element 40. Detection zone 630 can be positioned by the mechanism to translate the mask 440. According to various embodiments, as illustrated in FIG. 12D and described herein, the fluorescent light detection system can provide band 620 to a portion 540 of detector 290.

Figure 14:
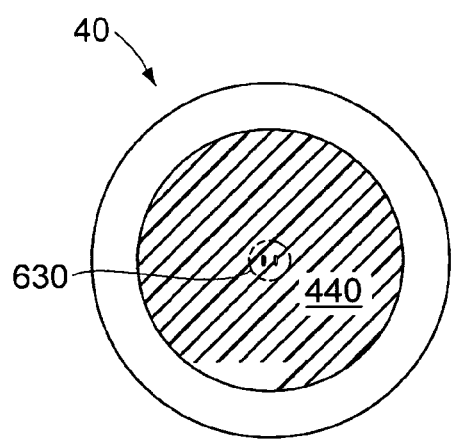
FIGS. 14-14A illustrate cross-sectional top views of various embodiments of a NA enhancing optical element and mask.
Figure 14A:
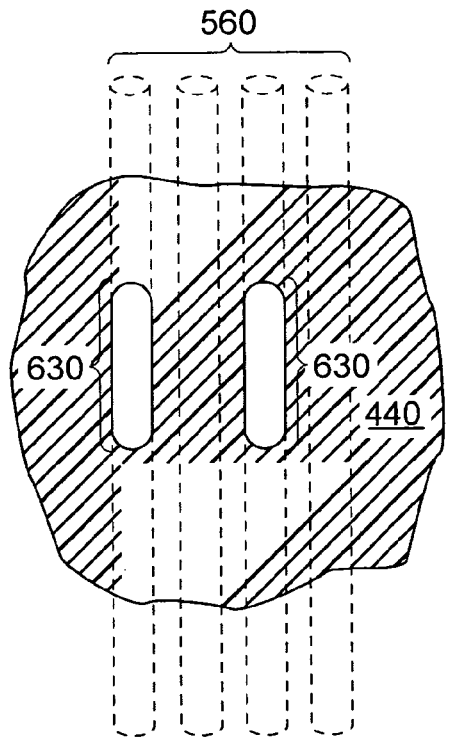
Figure 14B:
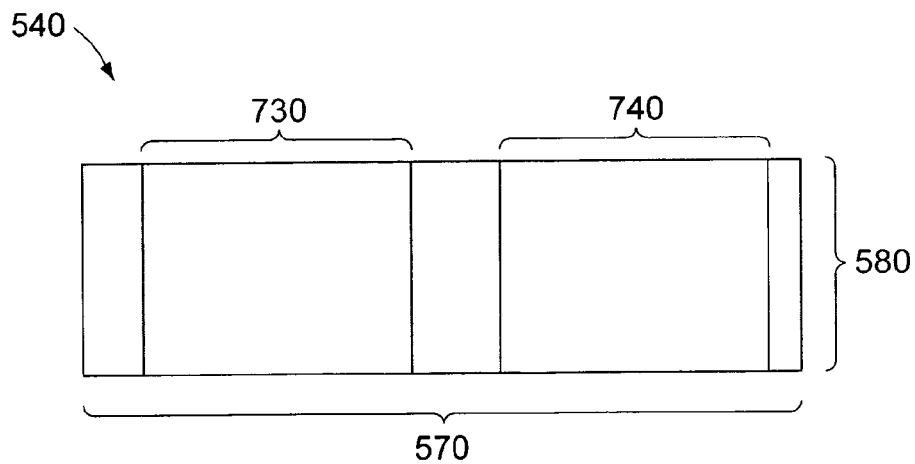
FIG. 14B illustrates a portion of a detector configured to detect fluorescent light collected from a first detection zone.

According to various embodiments, the fluorescent light detection system can collect fluorescent light from a subset of housings. According to various embodiments, the mask can include two or more apertures to provide multiple detection zones. According to various embodiments, the apertures can be aligned such that fluorescent light can be collected from non-adjacent housings. This can provide collection of fluorescent light from multiple housings. According to various embodiments, as illustrated in FIGS. 14 and 14A, mask 440 can include multiple detection zones 630. According to various embodiments, as illustrated in FIG. 14B, portion 540 of detector 290 can detect fluorescent light collected from a first detection zone as wavelength band 730 and from a second detection zone as wavelength band 740 without overlap. According to various embodiments, the fluorescent light detection system can include a dichroic mirror that provides bandpass filtering to reject wavelengths outside the range of interest to reduce overlap of wavelength bands.

Figure 15:
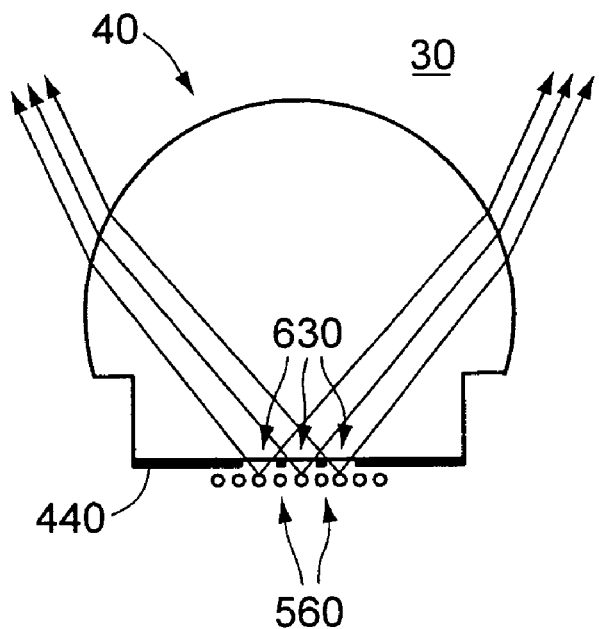
FIGS. 15-16 illustrate cross-sectional side views of various embodiments of NA enhancing optical element, mask, and housing configurations.
Figure 16:
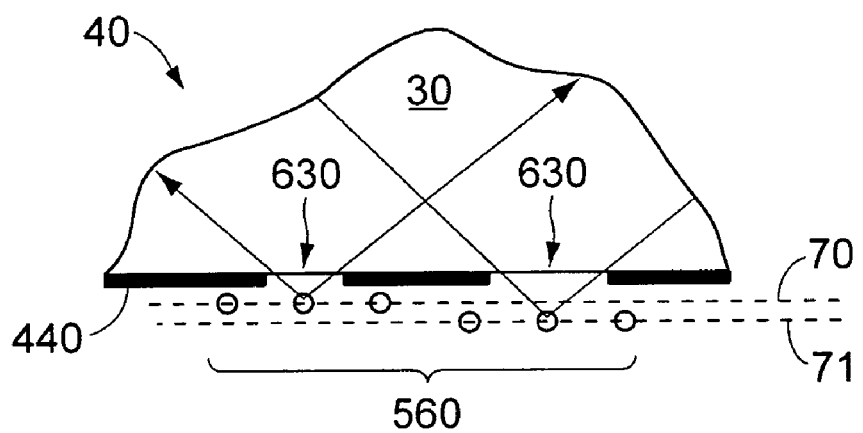

According to various embodiments, as illustrated in FIG. 15, mask 440 can include multiple apertures to provide detection zones 630 to collect fluorescent light 30 from non-adjacent housings 560. According to various embodiments, as illustrated in FIG. 16, mask 440 can include two apertures to provide detection zones 630 to collect fluorescent light 30 from non-adjacent housings 560. Housings 560 can be tilted from source plane 70 to source plane 71 to compensate for tilting detector 290 to reduce chromatic aberrations. According to various embodiments, the fluorescent light can be collected from the remaining housings by at least one of: (1) translating the housings 560; (2) translating the NA enhancing optical element 40 coupled to the mask 440; (3) translating the mask not coupled to the NA enhancing optical element 40 wherein the mask can be positioned between the housings 560 and NA enhancing optical element 40; and (4) translating the mask not coupled to the NA enhancing optical element 40 wherein the mask can be positioned between NA enhancing optical element 40 and detector 290.

According to various embodiments, the fluorescent light detection system can be included in an instrument for detection of fluorescent light from electrophoresis. According to various embodiments, the fluorescent light detection system can be included in an instrument for detection of fluorescent light from flow cytometry. According to various embodiments, the fluorescent light detection system can be included in an instrument for detection of fluorescent light from liquid chromatography, such as high-pressure liquid chromatography (HPLC).

According to various embodiments, a method for fluorescent light detection can include providing a plurality of housings for the samples, providing a NA enhancing optical element, providing a mask, and positioning the mask to reduce cross-talk between fluorescent light from the samples. According to various embodiments, positioning the mask can include positioning the mask between the NA enhancing optical element and the plurality of housings. According to various embodiments, positioning the mask further include translating the plurality of housings. According to various embodiments, positioning the mask can include translating the NA enhancing optical element and the mask. According to various embodiments, positioning the mask can include translating the mask. According to various embodiments, positioning the mask can include positioning the mask between the NA enhancing optical element and a detector.

Turning now to excitation of fluorescent light and coupling of an excitation light into a housing transporting a sample, exemplary embodiments of fluorescent light excitation systems and methods for exciting fluorescence employing coaxial illumination will now be described.

Figure 17A:
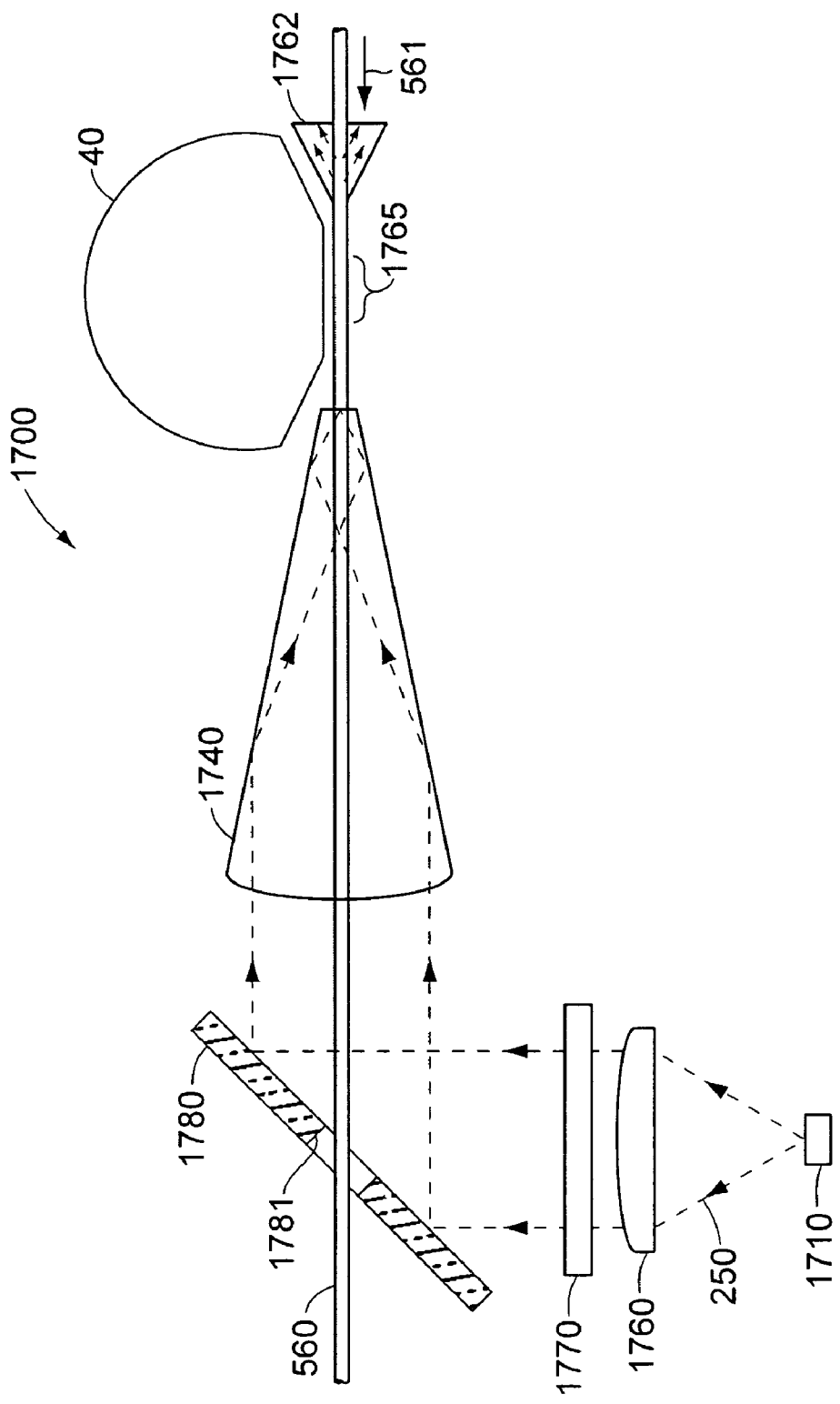
FIGS. 17A, 17B, and 17C illustrate a diagrammatical view of various embodiments of a fluorescent light detection system including a coupling optical element.

According to various embodiments, FIG. 17A illustrates an exemplary fluorescence excitation system 1700. Fluorescence excitation system 1700 can include a light source 1710, a lens 1760, a filter 1770, a reflecting optical element 1780, and a coupling optical element 1740. Light source 1710 can be a non-laser light source that provides non-coherent/incoherent illumination. A light source 1710 comprising a coherent source of illumination such as a laser light source may also be utilized in connection with various embodiments of the present teachings, however, non-coherent sources of illumination typically being more diffuse benefit readily from the enhanced capture and/or utilization of the illumination or intensity form such sources. Furthermore, the light source may comprise a combination coherent/non-coherent light source such as by way of example LED and laser light sources simultaneously or independently operating in the fluorescence excitation system 1700. Lens 1760 can be disposed proximate to light source 1710 to collect, collimate, and/or focus the non-coherent excitation light from light source 1710. Filter 1770 can be disposed between lens 1760 and reflecting optical element 1780. Filter 1770 can, for example, pass wavelengths of the non-coherent light useful for exciting fluorescence while removing wavelengths of the non-coherent light not useful for exciting fluorescence or wavelengths overlapping the collected fluorescent light.

In operation, referring to exemplary fluorescence excitation system 1700 in FIG. 17A, samples with dyes that can be excited to emit fluorescence can be transported through a detection zone 1765 by a housing 560. In various embodiments, housing 560 can be a capillary that can transport the sample within its lumen and serve as a waveguide for the excitation light. Housing 560 can have a circular cross-section, however, in various embodiments housing 560 can also have a non-circular cross-section. In certain embodiments, such as, for example, liquid chromatography, housing 560 can include a coating that exhibits different affinity for different components of the sample or a material, such as a gel or particulate, that provides a differential interaction with the components of the sample. In various embodiments, fluorescence excitation system 1700 can also include a light dump 1762 that, for example, can remove the excitation light from housing 560 to prevent bleaching of dyes before the sample enters detection zone 1765.

Lens 1760 can collect a non-coherent excitation light 250 from light source 1710 and can direct the collected non-coherent excitation light through filter 1770 towards reflecting optical element 1780. Filter 1770 can pass wavelengths of non-coherent excitation light useful for exciting the dyes to emit fluorescence and remove wavelengths of non-coherent light not useful for exciting the dyes to emit fluorescence or wavelengths overlapping the collected fluorescent light. Reflecting optical element 1780 can then collimate and direct the collected non-coherent excitation light towards coupling optical element 1740. The collimated non-coherent excitation light can enter the base of coupling optical element 1740. For ease of illustration, FIG. 17A shows light 250 bouncing twice within coupling optical element 1740 before being coupled into housing 560. Light 250, however, can be coupled into housing 560 after multiple bounces, one bounce, and zero bounces. In various embodiments, the geometry of coupling optical element 1740 can be configured such that light 250 bounces a number of times within coupling optical element 1740 before being coupled into housing 560, such that the acceptance angle of coupling optical element 1740 can be a fraction of the bounce angle of light 250 within coupling optical element 174. For example, light 250 can bounce once within coupling optical element 1740 before being coupled into housing 560. In this case, the acceptance angle of coupling optical element 1740 can be about one third of the bounce angle. Similarly, the geometry of coupling optical element 1740 can be configured such that light 250 bounces twice within coupling optical element 1740 before being coupled into housing 560, and the acceptance angle of coupling optical element 1740 can be about one fifth of the bounce angle. The geometry of coupling optical element 1740 can further be configured such that light 250 bounces three times within coupling optical element 1740 before being coupled into housing 560, and the acceptance angle of coupling optical element 1740 can be about one seventh of the bounce angle. In various embodiments, light 250 can bounce off the coupling optical element wall/air interface.

Due to the geometry of coupling optical element 1740, a portion of the non-coherent excitation light can pass through the wall of housing 560 and be coupled into housing 560 to propagate within housing 560 by total internal reflection. The non-coherent excitation light can propagate within housing 560 to illuminate detection zone 1765. A portion of detection zone 1765 can then be imaged by, for example, collection optics 40, as described above. After the non-coherent excitation light 250 illuminates detection zone 1765, light dump 1762 can allow the non-coherent excitation light to escape from housing 560 to avoid bleaching of dyes before reaching detection zone 1765.

Figure 18A:
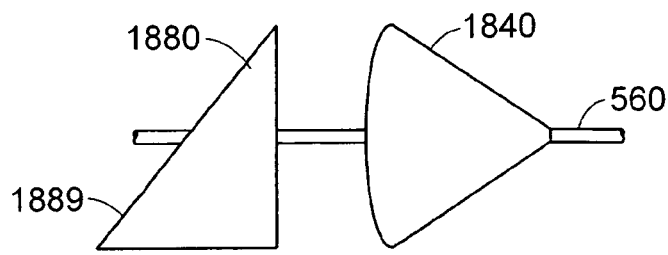
FIGS. 18A, 18B, 18C, and 18D illustrate side views of various embodiments of reflecting optical elements and coupling optical elements in a fluorescence excitation system.
Figure 18B:
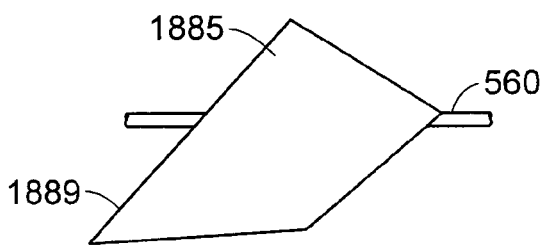
Figure 18C:
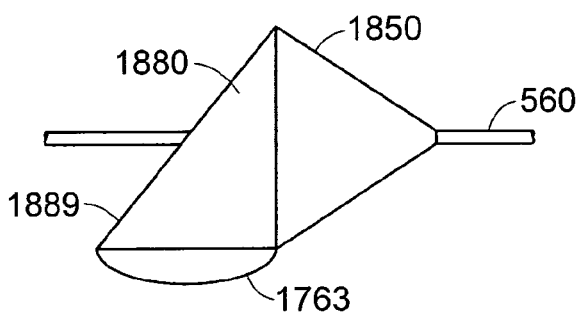
Figure 18D:
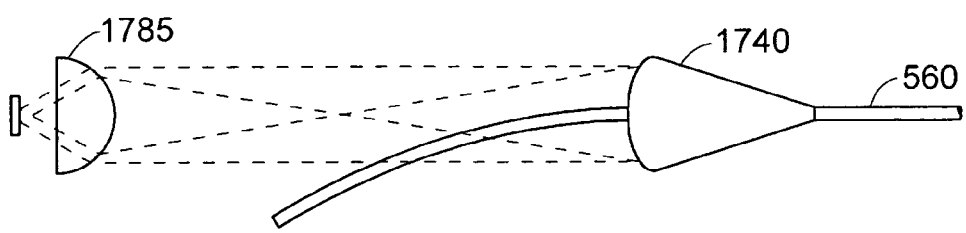

In various embodiments, reflecting optical element 1780 can be a flat mirror that can direct non-coherent light towards coupling element 1740. Reflecting optical element 1780 can also include a hole 1781 through which housing 560 can pass. In various embodiments, use of hole 1781 in reflecting optical element 1780 can be avoided by bending housing 560 at a location in the light path prior to coupling optical element 1740. An example of bending housing 560 to avoid the need for an aperture in a reflecting optical element 1780 is shown in FIG. 18D. According to various embodiments, as illustrated by FIG. 18A, the reflecting optical element can be a prism 1880 including a total internal reflection surface 1889 and an aperture through which housing 560 can pass. Prism 1880 can be positioned proximate to a coupling element 1840.

According to various other embodiments, reflecting optical element 1780 and coupling optical element 1740 can be a monolithic structure. As illustrated by FIG. 18B, a monolithic structure 1885 can integrate a prism including a total internal reflection surface 1889 with a coupling optical element 1885. According to still other embodiments, as illustrated by FIG. 18C, the reflecting optical element can be a prism 1880 including a total internal reflection surface 1889. Prism 1880 can be a separate structure from coupling optical element 1850, but disposed contacting coupling optical element 1840. As shown in FIG. 18C, a second lens 1763 can be positioned adjacent to prism 1880. Second lens 1763 can be, for example, a Fresnel, spherical, or aspheric lens. According to various embodiments, the reflecting optical element can collimate the non-coherent light before it enters the coupling optical element. In various other embodiments, a lens can focus the non-coherent light towards the coupling optical element. As shown in FIG. 18D, lens 1785 can focus the non-coherent light towards coupling optical element 1740. Housing 560 can also be bent to avoid the need for a hole in lens 1785.

Figure 17B:
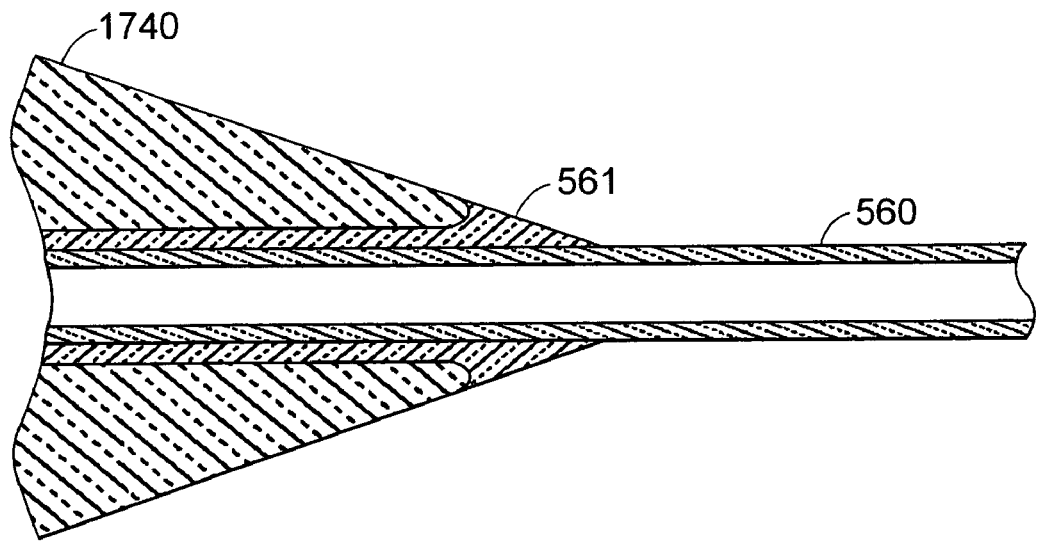

In various embodiments, coupling optical element 1740 can be a cone shaped element, an ob-round stretched cone shaped element, or a combination of the two shapes. Coupling optical element 1740 can be, for example, molded, cast, fused, heat shrunk, or press-fit onto housing 560. In various embodiments, an index matching compound or composition, such as, for example, an optical epoxy, can be used to optically couple coupling optical element 1740 and a portion of housing 560. The composition index matching compound may further be a solid material, a semisolid material, a liquid material, a viscous material, a gel material, or a combination thereof. Referring to FIG. 17B, coupling optical element 1740 can taper to an outer surface of housing 560 using, for example, an index matching compound 561.

Figure 17C:
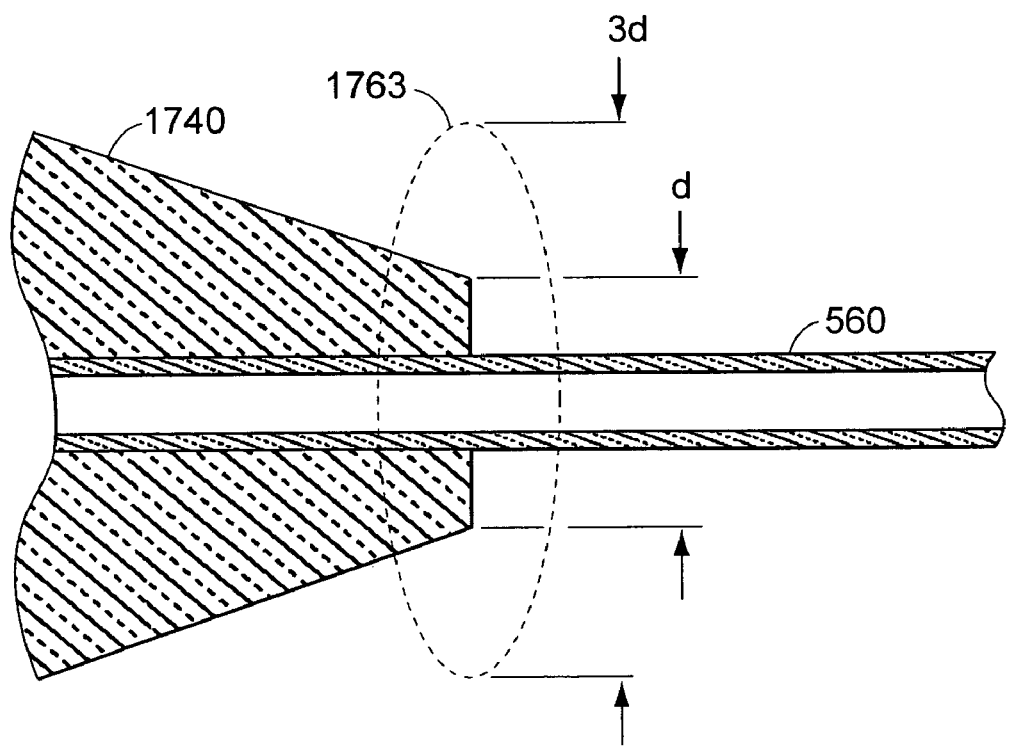

In various embodiments, coupling optical element 1740 does not taper to the outer surface of housing 560. Referring to FIG. 17C, coupling optical element 1740 does not taper to the outer surface of housing 560 but includes an end with a diameter d. Diameter d is larger than the diameter of the tip of coupling optical element 1740. Coupling optical element 1740 can function as desired if the excitation source image 1763 is appropriately larger than the diameter of the tip of coupling optical element 1740. For example, excitation source image 1763 can have a diameter of 3d, as shown in FIG. 17C.

In various embodiments, for example, in which the index of refraction of the material of coupling optical element 1740 is greater than the index of refraction of the material of housing 560, non-coherent light within coupling optical element 1740 and incident on housing 560 can propagate in one of the following modes. Light with a very shallow angle of incidence can reflect off an inner wall of housing 560 and not cross the lumen. Light with a shallow angle of incidence can enter the housing wall and propagate within the housing wall by total internal reflection. Light with a steep angle of incidence can enter and exit housing 560. And, light within a range of angles of incidence can pass through the outer surface of the housing wall and propagate within housing 560 in a general direction of the housing axis. Light within this range of angles of incidence can propagate in the housing wall and the lumen, reflecting off the outside housing wall. The angles that bound each of the above situations can depend on the index of refraction of the material of coupling optical element 1740 and the index of refraction of the material of housing 560. According to various embodiments, the cone shaped coupling optical element 1740 can have a cone angle within a range of angles in which illumination incident on housing 560 passes through the wall of housing 560 into the housing to propagate in a direction of the housing axis by total internal reflection.

In various embodiments, the index matching compound 561 may fill or occupy a space or region between the coupling optical element 1740 and the housing 560. The index matching compound 561 may further be selected to possess desirable optical properties that influence the coupling efficiency of light propagating from the coupling optical element 1740 and the housing 560. For example, the index matching compound 561 may have a refractive index that improves the coupling efficiency between the coupling optical element 1740 and the housing 560.

In various embodiments, the refractive index of the index matching compound 561 may be less than that of the coupling optical element 1740. Providing a differential between the refractive index of the index matching compound 561 and the coupling optical element 1740 may further improve coupling efficiency between the coupling optical element 1740 and the housing 560, the coupling optical element 1740 and the index matching compound 561, or the coupling optical element 1740 and the housing 560. In a similar manner, the refractive index of the index matching compound 561 may be selected on the basis of the optical properties or refractive index of the housing 560 to achieve a desired coupling efficiency.

In various embodiments, the refractive index of the index matching compound 561 may be selected to be in the approximate range of between 1.4 and the refractive index of the coupling optical element 1740. In various embodiments, the refractive index of the index matching compound 561 may be slightly more or less than 1.4 or significantly more or less than 1.4. Additionally, the refractive index of the index matching compound 561 may be slightly more or less than the coupling optical element 1740 or significantly more or less than the coupling optical element 1740.

Figure 17D:
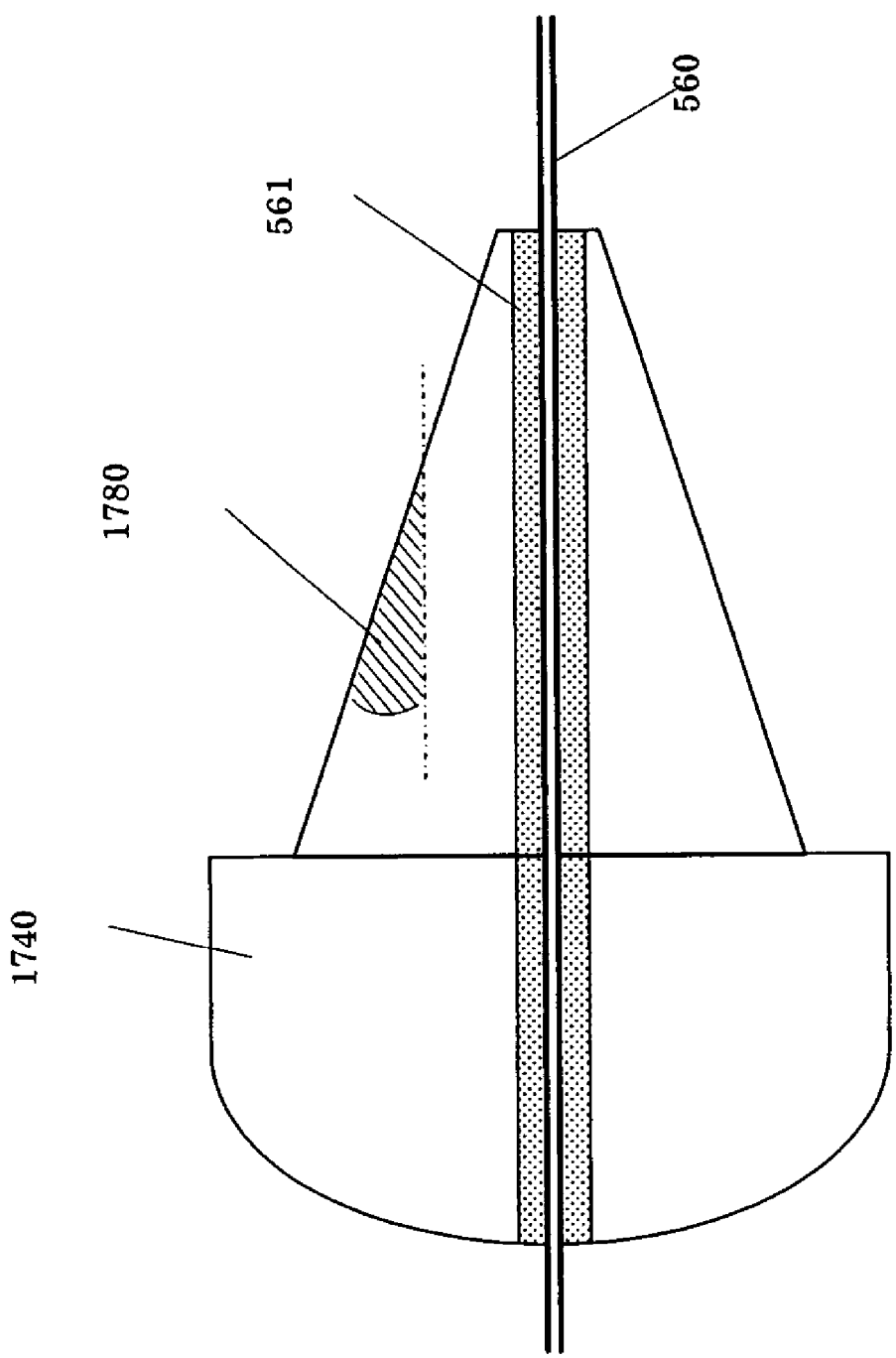
FIGS. 17D and 17E illustrate principals of coupling efficiency and index matching characteristics in the light detection system.
Figure 17E:
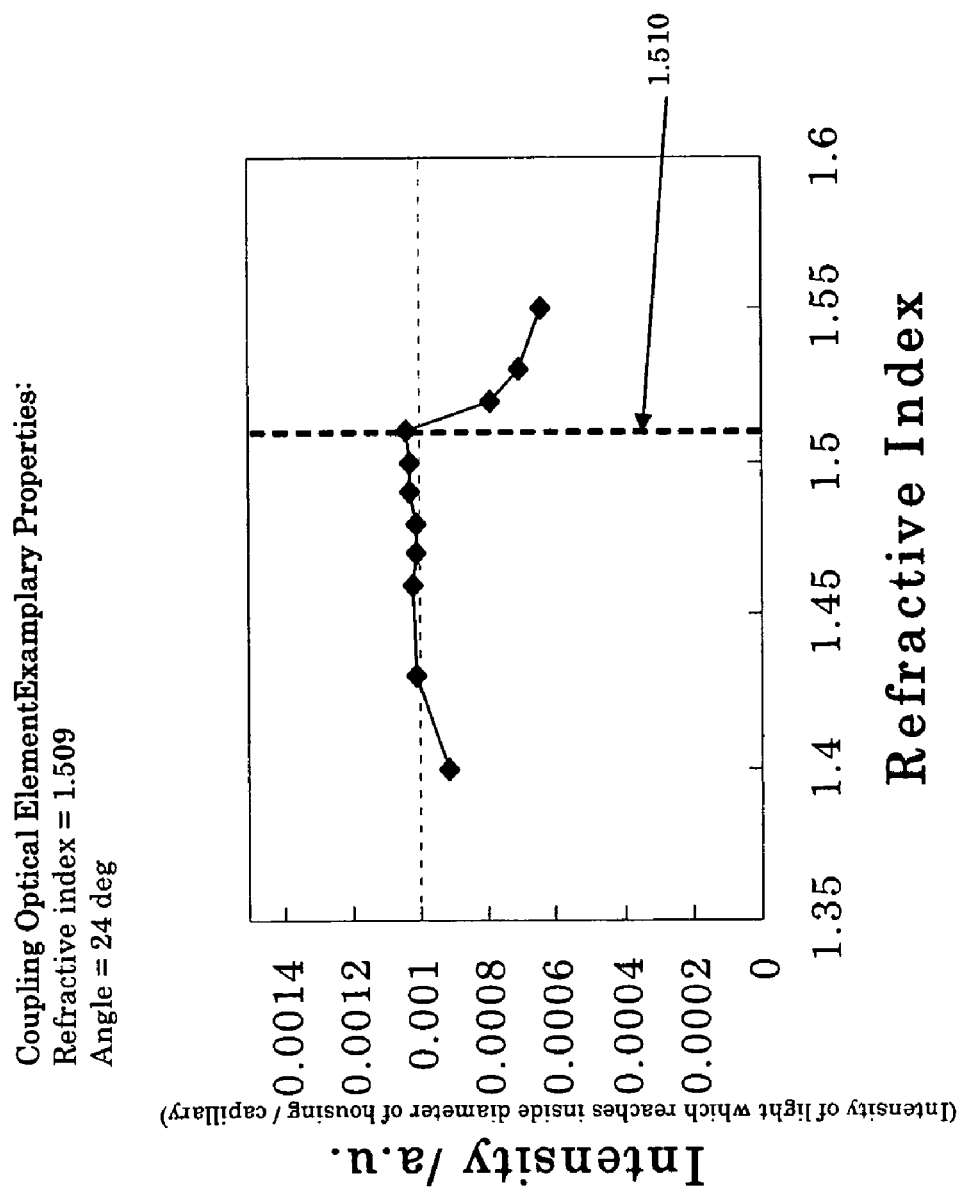

FIGS. 17D-E illustrate one embodiment of the relationship between the coupling optical element 1740 and the housing 560 wherein the index matching compound 561 resides therebetween to achieve a desired coupling efficiency. In one aspect, the coupling efficiency between the coupling optical element 1740 and the housing 560 may be evaluated based on the optical properties of each to determine the appropriate or desired refractive index for the index matching compound 561. For example, FIG. 17E illustrates an exemplary dependence of coupling efficiency between the coupling optical element 1740 and the housing 560 for a coupling optical element having a refractive index of approximately 1.5 and an angle 1780 of approximately 24 degrees. The coupling efficiency may further be determined as a function of the intensity of emission or percentage of propagation through the coupling optical element 1740 to the housing 560. Using this information an appropriate or desired refractive index for the index matching compound 561 can be determined.

Figure 25A:
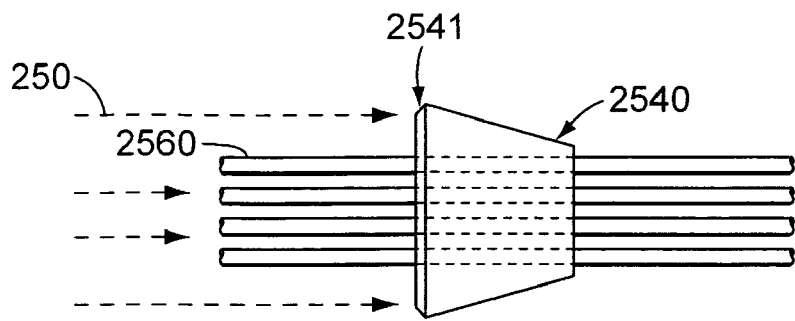
FIGS. 25A, 25B, and 25C illustrate exemplary coupling optical elements and housings in accordance with embodiments of the fluorescence excitation system.
Figure 25B:
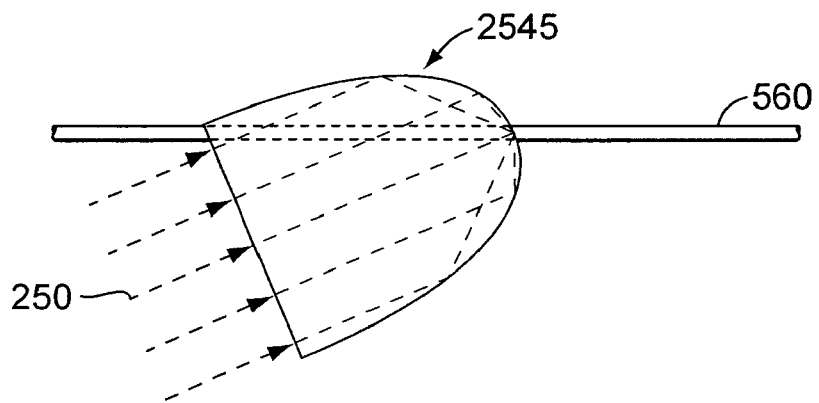
Figure 25C:
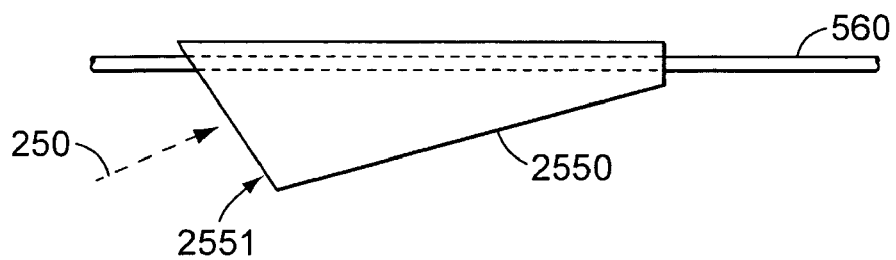

In various embodiments, the coupling optical element can be any shape that facilitates coupling of light into housing 560. Referring to FIG. 25A, a coupling optical element 2540 can, for example, have an axial asymmetric shape, such as a cone with an ob-round cross section, to couple to a plane of capillaries 2560. Light 250 can enter into an end 2541 of coupling optical element 2540 and then coupled into the plane of capillaries 2560. According to various other embodiments, the coupling optical element can have an ellipsoidal or parabolic shape. Referring FIG. 25B, a coupling optical element 2545 has an ellipsoidal or parabolic shape that can couple light 250 into a planar end. Light 250 can then be coupled into housing 560. According to still other embodiments, a coupling optical element 2550 can have an wedge or truncated conical shape. Referring to the side view of FIG. 25C, a coupling optical element 2550 can have a wedge shape that can couple light 250 into an end 2551. Light 250 can then be coupled into housing 560.

Figure 19A:
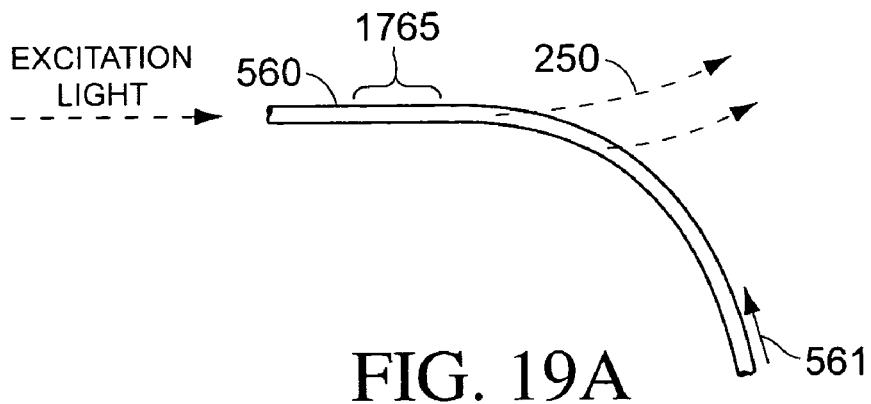
FIGS. 19A, 19B, and 19C illustrate diagrammatical views of various embodiments of a light dump in a fluorescence excitation system.
Figure 19B:
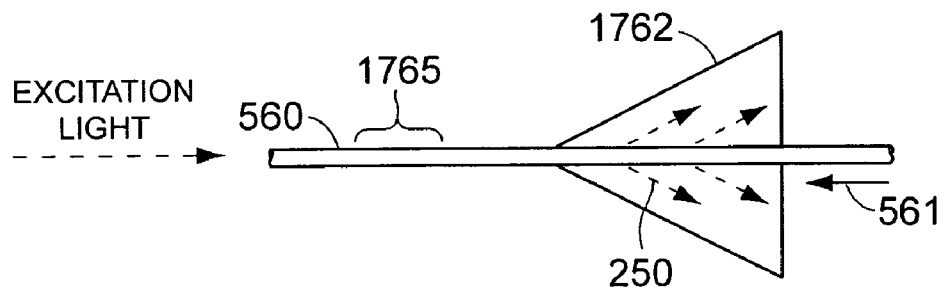
Figure 19C:
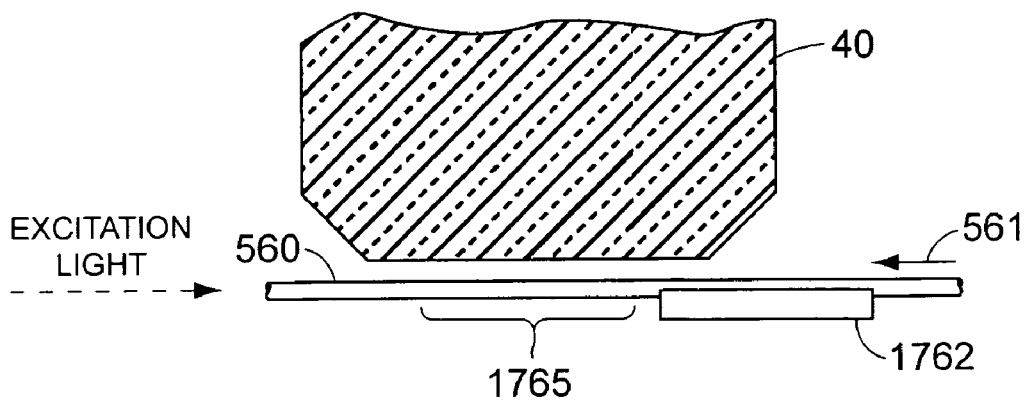

In various embodiments, a light dump 1762 can absorb or transmit the excitation light. For example, light dump 1762 can be a low fluorescence absorbing material and can be positioned away from the optics path. For example, light dump 1762 can be a black paint, an epoxy, or a charred polyimide that absorbs the non-coherent excitation light. In various other embodiments, the light dump can be, for example, a curved section of housing 560 that permits excitation light 250 to escape, as shown in FIG. 19A. Curved section of housing 560 can be positioned after light 250 passes detection zone 1765. In various embodiments, curved section of housing 560 can be positioned before the sample reaches detection zone 1765, as depicted in FIG. 19A by arrow 561 showing the direction of sample flow within housing 560. As shown in FIG. 19B, light dump 1762 can be a conical element made of a material with an index equal to or greater than an index of the fluid in the lumen of housing 1760, to allow non-coherent excitation light 250 to escape from housing 1760. The shape of light dump 1762 can vary as necessary to accommodate the shape of housing 560. In various embodiments, as shown in FIG. 19C, light dump 1762 can be optically coupled to the sample housing less than the full circumference of housing 560 to facilitate dumping excitation light 250 closer to detection zone 1765 in the presence of, e.g. collection optics 40 which can be in close proximity to housing 560.

Figure 20:
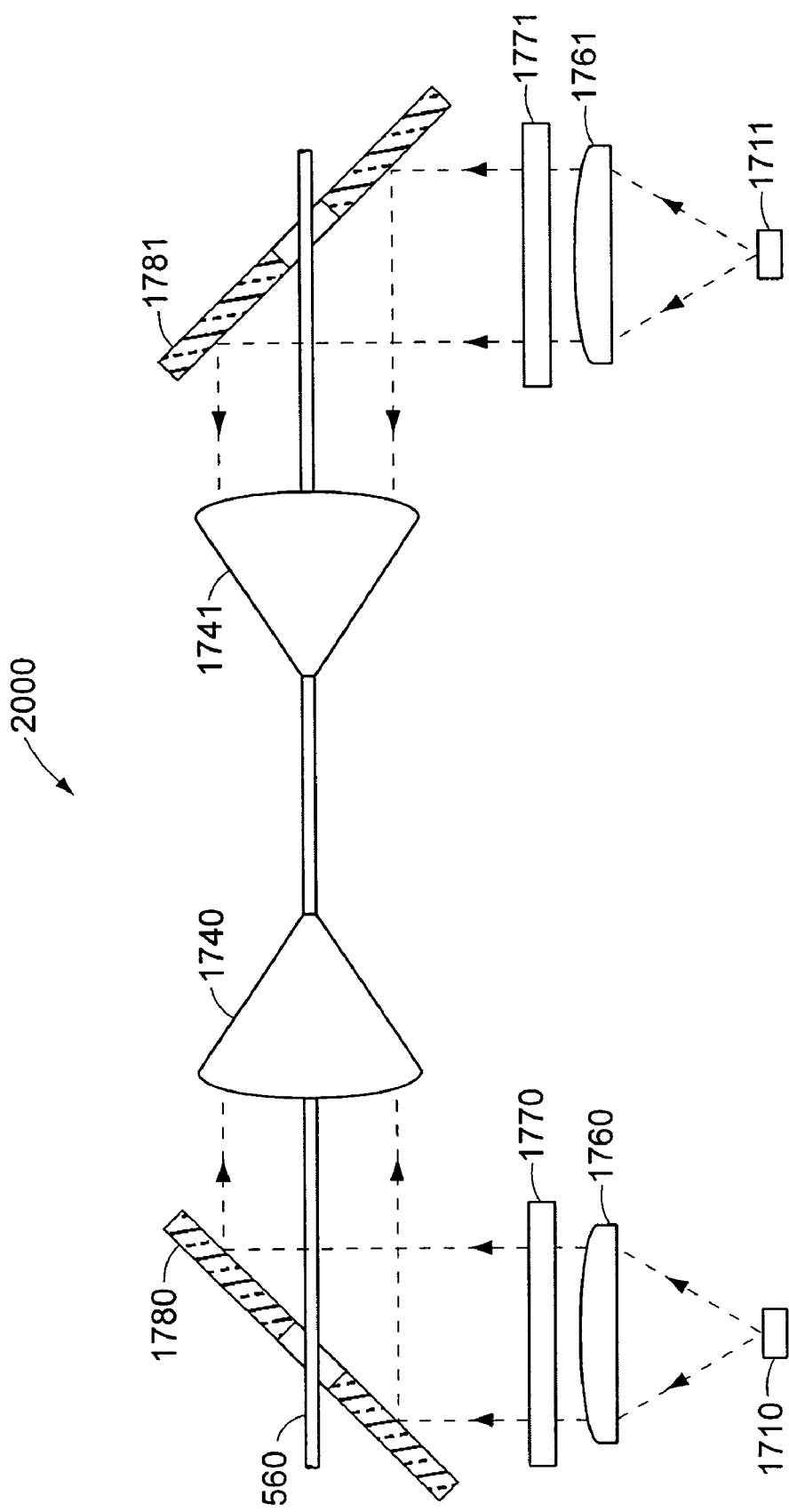
FIG. 20 illustrates a diagrammatical view of various embodiments of a fluorescence excitation system.

According to various embodiments, an exemplary fluorescence excitation system can include multiple non-coherent light sources and coupling optical elements. Referring to FIG. 20, fluorescence excitation system 2000 can include a light source 1710, a lens 1760, a filter 1770, a reflecting optical element 1780, and a coupling optical element 1740. In various embodiments, fluorescence excitation system 2000 can further, include a second light source 1711, a second lens 1761, a second filter 1771, a second reflecting optical element 1781, and a second coupling optical element 1741. Second light source 1711 can be a non-laser light source that provides non-coherent illumination. In various embodiments, the coupling optical elements can be used as light dumps. For example, coupling optical element 1741 can be a light dump for non-coherent illumination from light source 1710, and coupling optical element 1740 can be a light dump for non-coherent illumination from light source 1711.

Figure 21:
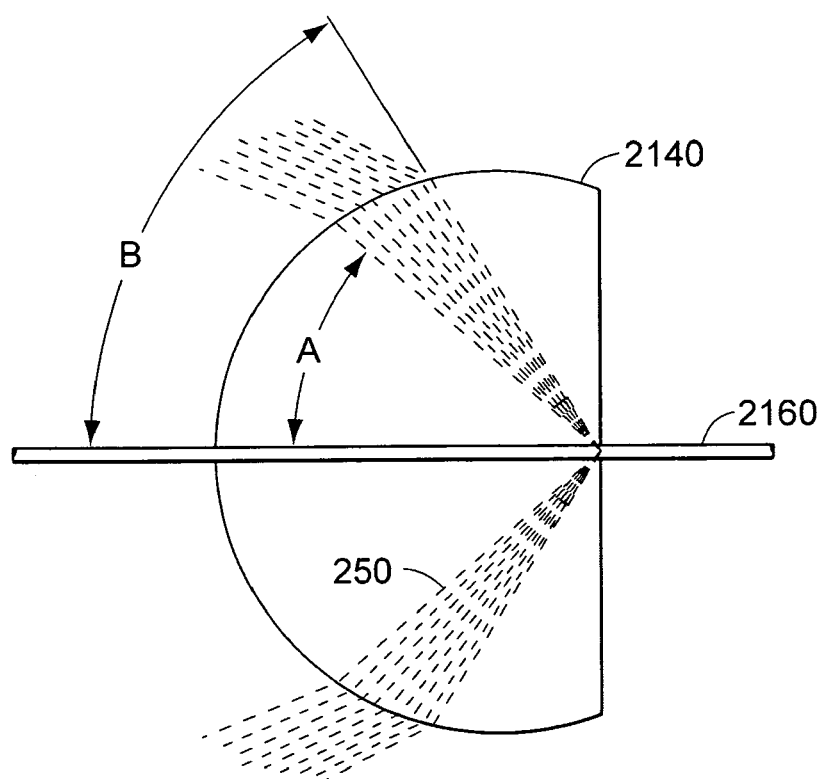
FIG. 21 illustrates a side view of various embodiments of a coupling optical element.

According to various embodiments, the coupling optical element can be a truncated sphere, similar in shape to NA enhancing element 40 shown in FIG. 3A. Referring to FIG. 21, a truncated sphere 2140 can be used as a coupling optical element to direct non-coherent excitation light 250 through a wall of housing 2160 to coaxially propagate. Coupling of non-coherent excitation light through the walls of the housing 2160 provide a mechanism by which to provide axially propagating light without the requirement that such light be introduced into the housing 2160 via its terminus or end.

In various embodiments, truncated sphere 2140 can be molded, cast, fused or optically connected onto housing 2160. In various embodiments, excitation light incident on housing 2160 at an angle less than A will reflect off the inner wall of housing 2160 and remain in the wall as it propagates. Excitation light incident on housing 2160 at an angle greater than B will not reflect off housing 2160 and exit housing 2160. However, excitation light 250 that is incident at an angle greater or equal to A and less than or equal to B can coaxially propagate along the axis of housing 2160. For example, in an exemplary embodiment, truncated sphere 2140 can have an index of refraction of 1.85, housing 2160 can have an index of refraction of 1.46, and a fluid in housing 2160 can have an index of refraction of 1.41. Excitation light incident at 40.6° or more and 57.4° or less can coaxially propagate and illuminate the fluid in the lumen of the housing.

Figure 22:
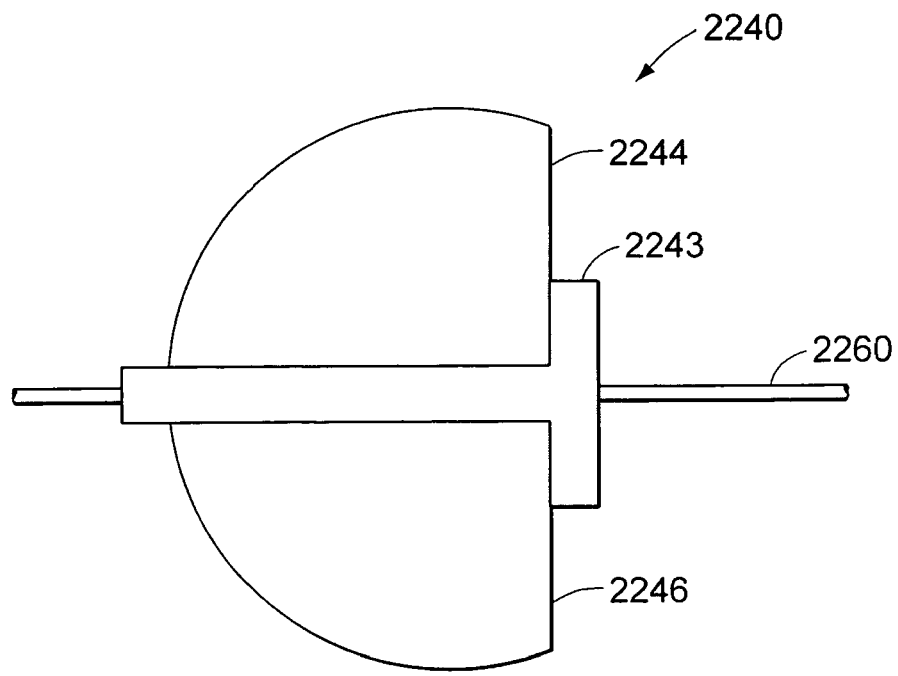
FIG. 22 illustrates a side view of various embodiments of a coupling optical element.

In various embodiments, the coupling optical element can comprise a plurality of optical elements. FIG. 22 shows a side view of a coupling optical element 2240 that can include a transparent element 2243 that can be molded, cast, fused or optically connected onto housing 2260. On a first, or top surface of a transparent element 2243, a portion of a sphere 2244 can be joined to transparent element 2243 by, for example, and index matching compound or fluid. Similarly, a second portion of a sphere 2246 can be joined to a second, or bottom surface of transparent element 2243. Collectively, transparent element 2243, portion of a sphere 2244, and second portion of a sphere 2246 form coupling optical element 2240 to coaxially propagate non-coherent excitation light in housing 2260.

Figure 23:
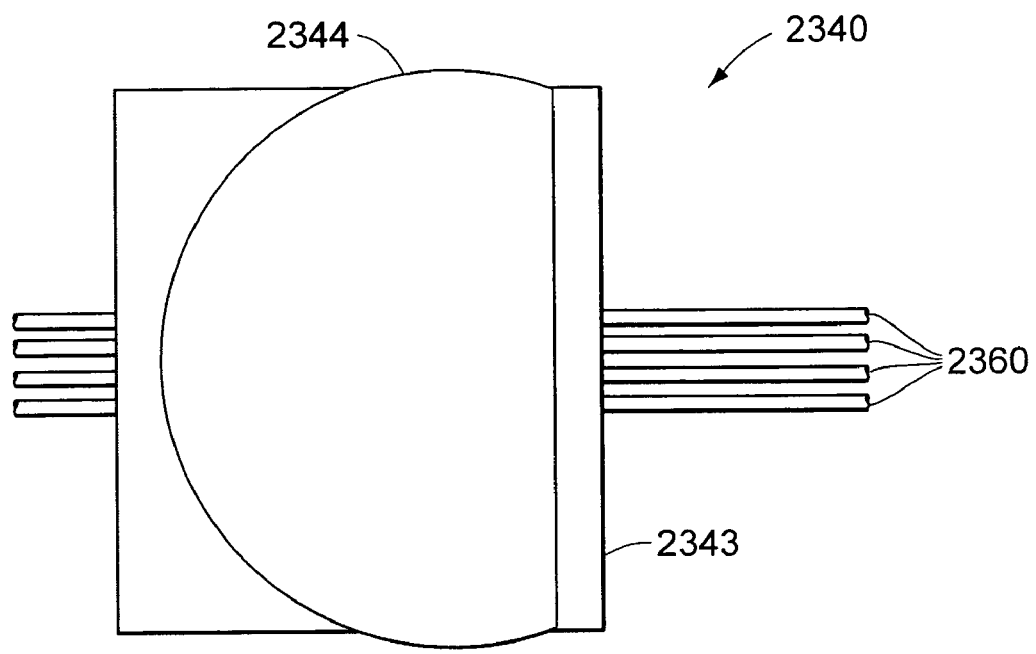
FIG. 23 illustrates a top view of various embodiments of a coupling optical element.

In various embodiments, the housing can include a plurality of capillaries. As shown in FIG. 23, a plurality of capillaries 2360 can transport a sample to a detection zone. A transparent element 2343 can be molded, cast, or fused onto plurality of capillaries 2360 to couple a non-coherent excitation light to coaxially propagate in plurality of capillaries 2360. A portion of a sphere 2344 can be joined, for example by an index matching compound or fluid, to a first surface, or top surface of transparent element 2343. A second portion of a sphere, shown in FIG. 22 can be joined, for example by an index matching compound or fluid, to a second surface, or bottom surface of transparent element 2343. Collectively, transparent element 2343, portion of a sphere 2344, and the second portion of a sphere, shown in FIG. 22, form coupling optical element 2340 to coaxially propagate non-coherent excitation light in the plurality of capillaries 2360.

In various embodiments including a plurality of capillaries, barriers can be used to reduce cross-talk between the capillaries. As shown in the end view of FIG. 29, each a plurality of capillaries 2960 can be separated by a barrier 2961. Barrier 2961 can be an opaque material that reduces cross-talk between capillaries 2960.

Figure 24:
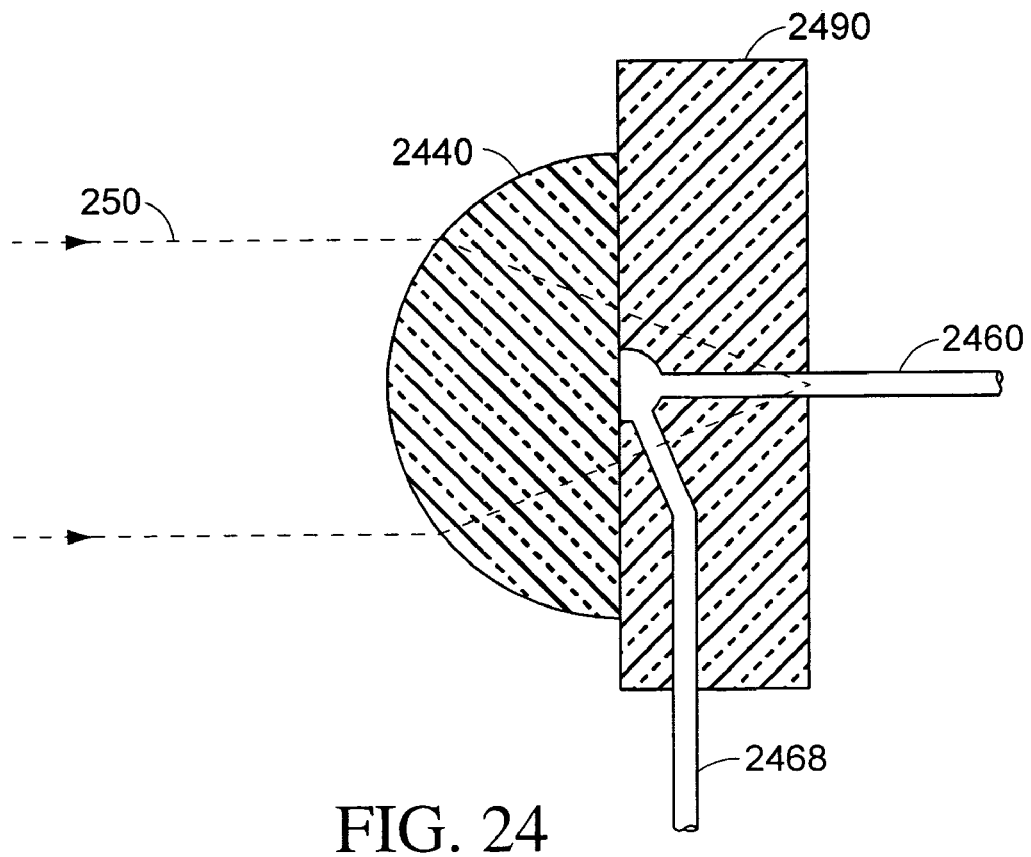
FIG. 24 illustrates a diagrammatical view of various embodiments of a fluorescence excitation system.

Coaxial illumination can further be accomplished by coupling non-coherent light to an end of a housing. According to various embodiments, the coupling optical element can be a truncated sphere or hemisphere, similar in shape to NA enhancing element 40 shown in FIG. 3A, that focuses non-coherent light to the end of the housing while still permitting a fluid connection to the end of the housing. Referring to the cross-sectional view of FIG. 24, a truncated sphere 2440 can serve as a coupling optical element. An optically transparent seal 2490 that facilitates fluid transfer from a fluid connection 2468 to a housing 2460 can be connected between fluid connection 2468 and housing 2460. Truncated sphere 2440 can be joined to seal 2490, as shown in FIG. 24, so that fluid can be transferred from fluid connection 2468 to housing 2460, and so that truncated sphere 2240 can collect non-coherent light 250 and focus it to an end of housing 2460.

Figure 26:
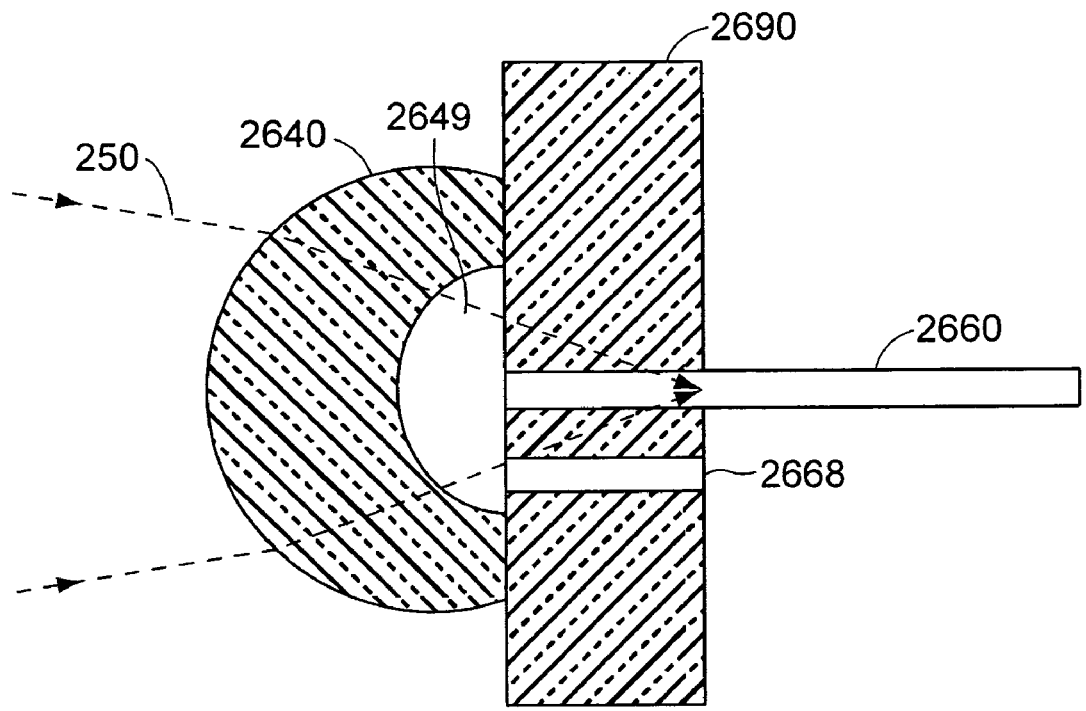
FIG. 26 illustrates a diagrammatical view of various embodiments of a fluorescence excitation system.
Figure 27:
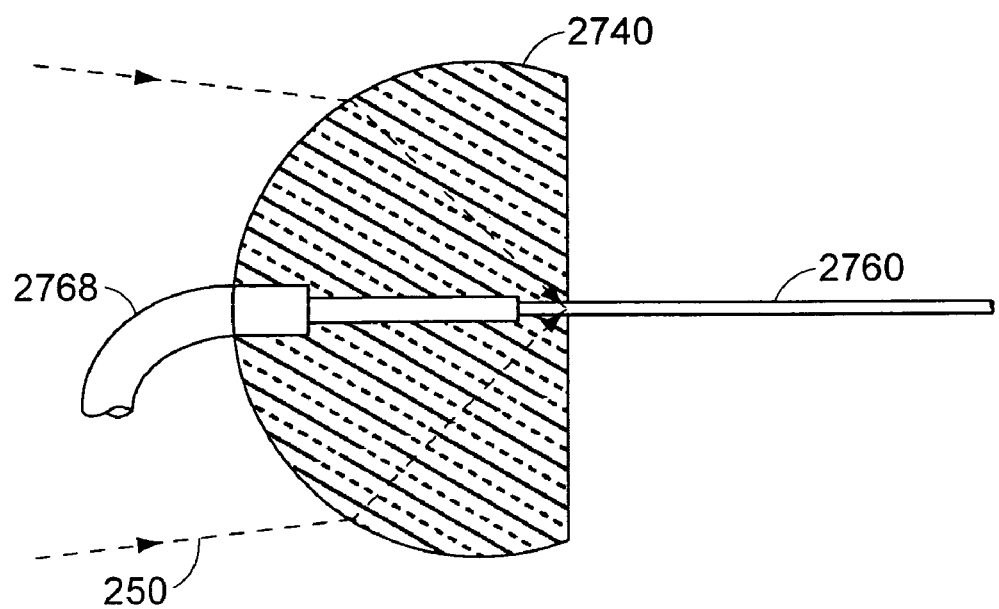
FIG. 27 illustrates a diagrammatical view of various embodiments of a fluorescence excitation system.

According to various embodiments, the coupling optical element can include a meniscus lens. Referring to FIG. 26, the coupling optical element can be a meniscus lens 2640 joined to a transparent element 2690. The joined meniscus lens 2640 and transparent element 2690 can form a cavity 2649. Transparent element 2690 can further include a fluid connection 2668 to allow fluid flow into cavity 2649. A housing 2660 can pass through a width of transparent element 2690 so that an end of housing 2660 can open within cavity 2649 to allow fluid flow into housing 2660. Fluid transporting a sample can flow from fluid connection 2668 into cavity 2649 and then from cavity 2649 into the end of housing 2660. A detection zone portion of housing 2660 (not shown) can be illuminated coaxially using meniscus lens 2640 to collect non-coherent excitation light 250 and focus it onto the end of housing 2660 that opens into cavity 2649.

According to various embodiments, the coupling optical element can be a truncated sphere joined to the housing. As shown in the cross-sectional view of FIG. 27, a truncated sphere 2740 can be joined to a housing 2760 by, for example, molding, casting, or fusing. A fluid connection 2768 can be joined to truncated sphere 2740 so that fluid can pass through truncated sphere 2740 and enter an end of housing 2760. A detection zone portion of housing 2760 (not shown) can be illuminated coaxially using truncated sphere 2740 to collect non-coherent excitation light 250 and focus it onto the end of housing 2760.

Figure 28:
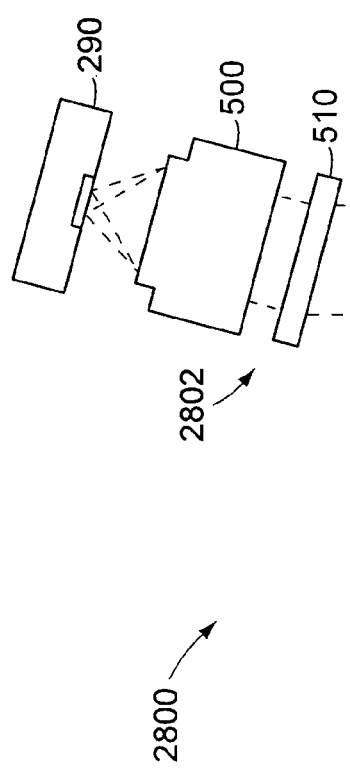
FIG. 28 illustrates a diagrammatical view of various embodiments of a fluorescence excitation and detection system.

According to various embodiments, a system for analyzing biological samples can include a fluorescence excitation system and a fluorescence detection system. Referring to FIG. 28, a system 2800 for analyzing biological samples can include an exemplary fluorescence excitation system 2801 with multiple non-coherent light sources and coupling optical elements. As shown in FIG. 28, fluorescence excitation system 2801 can include a light source 2810, a lens 2860, a filter 2870, a reflecting optical element 2880, and a coupling optical element 2840. In various embodiments, fluorescence excitation system 2801 can also include a second light source 2811, a second lens 2861, a second filter 2871, a second reflecting optical element 2881, and a second coupling optical element 2841. Second light source 2811 can be a non-laser light source that provides non-coherent illumination. Samples can be transported to a detection zone by a housing 560. In various embodiments, housing 560 can comprise a plurality of capillaries.

System 2800 for analyzing biological samples can further include an exemplary fluorescent light detection system 2802 including a NA enhancing optical element 40, lenses 430 and 500, a mask (not shown), a grating 510, and a detector 290. Grating 510 can refract light in a direction perpendicular to the axis of housing 560, for example, in a direction into or out of the page. For ease of illustration, this is depicted in FIG. 28 by the slight tilting of grating 510 and lens 500. According to various embodiments, a mirror can be positioned to direct where the image falls on the detector. According to various embodiments, the detector can be masked to control where the image falls on the detector. According to various embodiments, housing 560 can include a plurality of capillaries and/or grating 510 can be replaced by a filter wheel. The filter wheel can be selected to provide good spectral separation and collection efficiency allowing differentiation between multiple dyes within a sample.

In operation, light sources 2810 and 2811 can provide excitation light to lenses 2860 and 2861, respectively. The excitation light can be directed to filters 2870 and 2871, respectively, that can condition the excitation light by accepting desirable wavelengths of excitation light while blocking other wavelengths. The excitation light can be reflected by reflecting elements 2880 and 2881, respectively, and directed to optical coupling elements 2840 and 2841, respectively. The excitation light can be coupled to housing 560 to propagate coaxially. The excitation light can be absorbed by dyes in the samples in housing 560, stimulating the dyes to emit fluorescent light 30 in all directions. According to various embodiments, NA enhancing optical element 40 can collect fluorescent light 30 from the detection zone and direct it to lens 430. The fluorescent light can be dispersed by transmission grating 510, and focused by lens 500 onto detector 290. One of skill in the art will understand that the system for analyzing samples described above is exemplary, and that other excitation systems disclosed herein can be combined with the other detection systems disclosed herein.

Figure 29A:
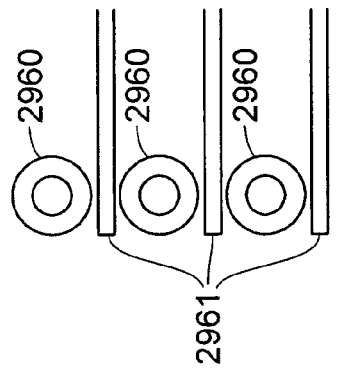
FIG. 29A illustrates a diagrammatical view of various embodiments of a fluorescence excitation and detection system including multiple capillaries with barriers to reduce crosstalk.

In various other embodiments, housing 2860 can comprise a plurality of lumens, such as, for example, a multi-bore capillary or multi-channel plate. In various other embodiments, housing 2860 can comprise multiple housings with a single or multiple lumens in each housing. In embodiments including multiple capillaries, such as, for example, shown in FIG. 25A, barriers can be positioned to reduce cross-talk between capillaries. FIG. 29A shows multiple capillaries 2960 can be separated by barriers 2961. Barriers 2961 can restrict the excitation light and/or fluorescent light to one capillary.

Figure 29B:
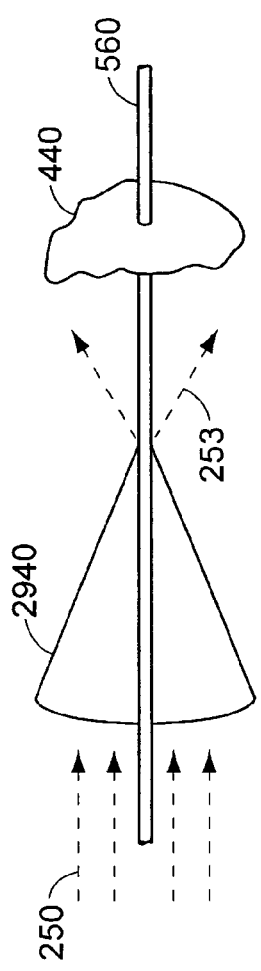
FIG. 29B illustrates a diagrammatical view of various embodiments of a mask to reduce stray light from a detection zone and/or detection optics.

In various embodiments, a mask can be used to protect the detection zone and detection optics from stray excitation light. Referring to FIG. 29B, a mask 440 can be positioned around housing 560 downstream of a coupling optical element 2940. Mask 440 can be, for example, an opaque material including a slit to allow insertion of mask 440 onto housing 560. An excitation light 250 can be coupled into housing 560 by coupling optical element 2940. A portion of the light, stray light 253, will not be coupled into housing 560 and will exit coupling optical element 2940, as shown in FIG. 29B. Mask 440 can protect the detection zone and detection optics from stray light 253.

Figure 30:
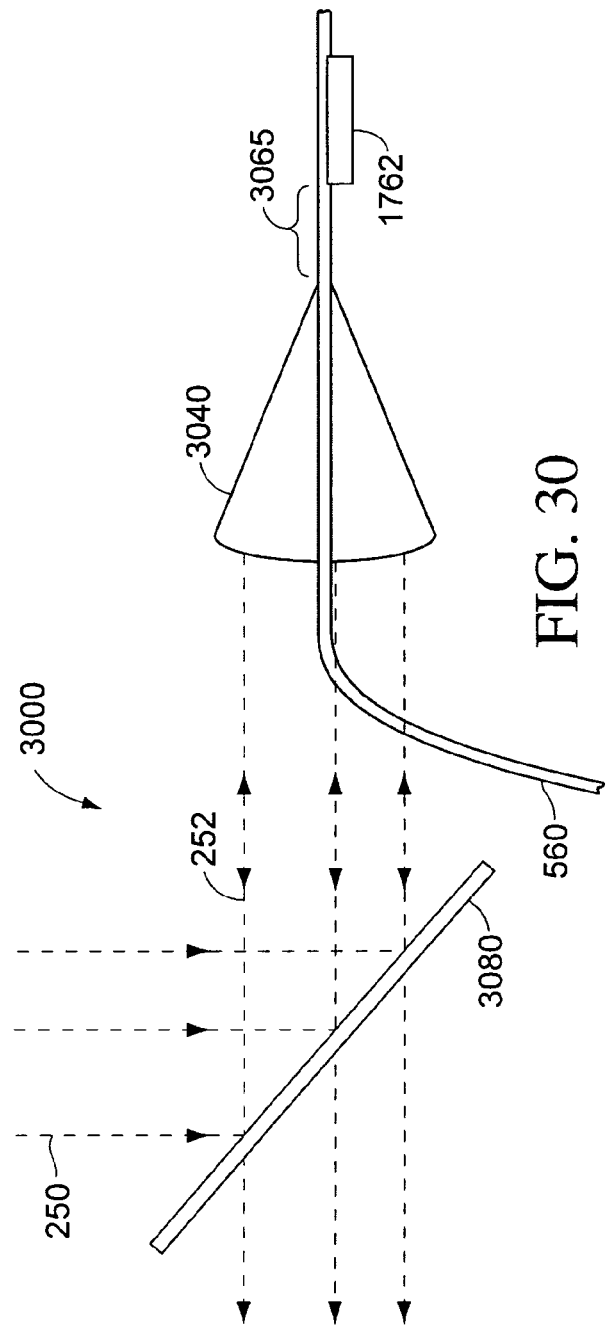
FIG. 30 illustrates a diagrammatical view of various embodiments of a system including a coupling optical element to couple light into and out of a housing.

According to various other embodiments, a system can include a coupling optical element to couple light into and out of a housing. Referring to FIG. 30, a system 3000 can include a light source to provide a light 250, an optical element 3080, and a coupling optical element 3040. Optical element 3080 can be, for example, a dichroic optical filter. Optical element 3080, such at the dichroic optical filter, is shown in FIG. 30 positioned at a 45 degree angle relative to excitation light 250. One of ordinary skill in the art understands, however, that other angles can be used. System 3000 can further include a housing 560, such as, for example, a capillary. Housing 560 can be bent to avoid optical element 3080. Coupling optical element 3040 can be coupled to housing 560 as disclosed herein. In various embodiments, system 3000 can further include a light dump 1762.

In operation, excitation light 250 can reflect from optical element 3080 and be directed towards coupling optical element 3040. Coupling optical element 3040 can then couple excitation light 250 into capillary 560. Once coupled into capillary 560, excitation light 250 can be interact with samples in housing 560 at a zone 3065 and cause fluorescent light to be emitted in all directions. A portion of the fluorescent light will be emitted towards coupling optical element 3040. Coupling optical element 3040 can then couple that portion of the fluorescent light out of housing 560 and direct it towards optical element 3080. The fluorescent light coupled out of housing 560 and directed towards optical element 3080 by coupling optical element 3040 is shown as fluorescent light 252 in FIG. 30. Optical element 3080, such as, for example, the dichroic optical filter can allow fluorescent light 252 to pass, but reflect non-desirable wavelengths of light, such as, excitation light 250. Fluorescent light 252 can then be directed towards a detector (not shown).

Figure 31:
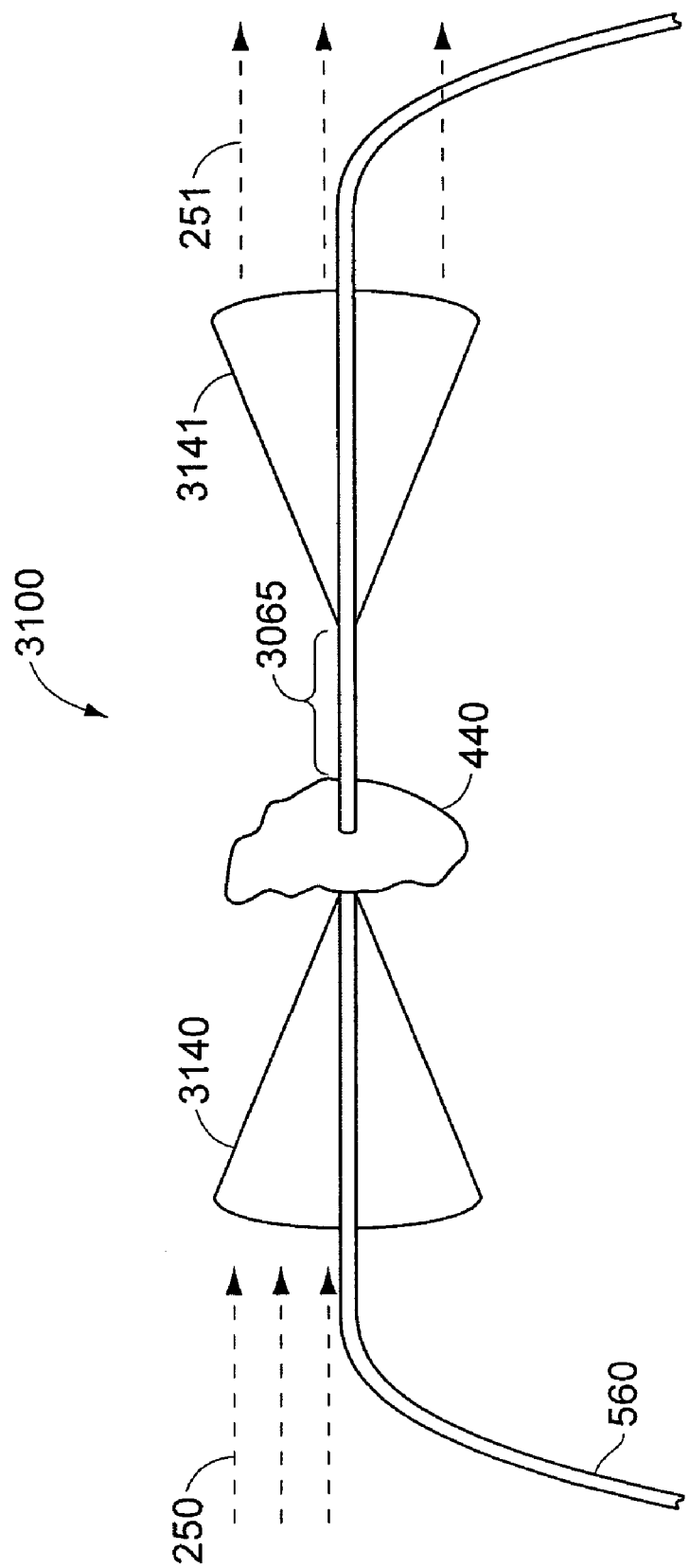
FIG. 31 illustrates a diagrammatical view of various embodiments of an absorbance and/or fluorescence system.

In still other embodiments, an absorbance and/or fluorescence system is provided that can be used in, for example, a liquid chromatography system. Referring to FIG. 31, an absorbance system 3100 can include a light source that provides an excitation light 250, a first coupling optical element 3140, a second coupling optical element 3141, a mask 440, and a housing 560. Housing 560 can be bent as shown in FIG. 31 to avoid the light source (not shown) and the detector (not shown). One of ordinary skill in the art understands, however, that housing 560 can be bent in other manners, such as, for example, in the shape of a Z. First coupling optical element 3140 and second coupling optical element 3141 can be coupled to housing 560 as disclosed herein.

Figure 32A:
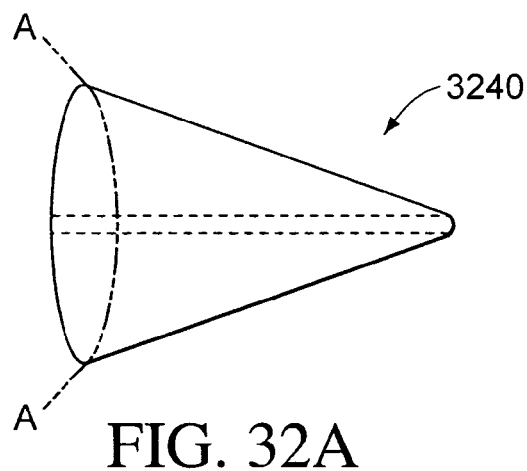
FIGS. 32A-C illustrate diagrammatical views of various embodiments of a coupling optical element comprising a plurality of sections.
Figure 32B:
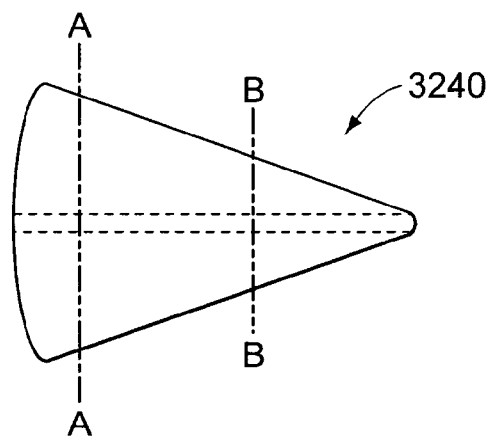
Figure 32C:
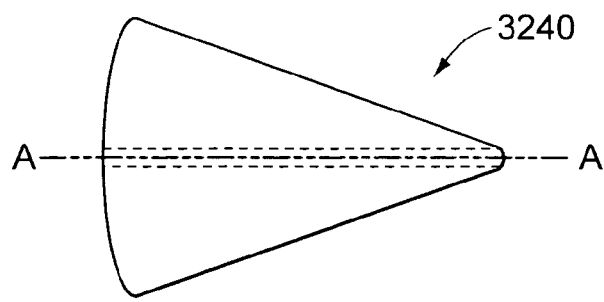
Figure 33:
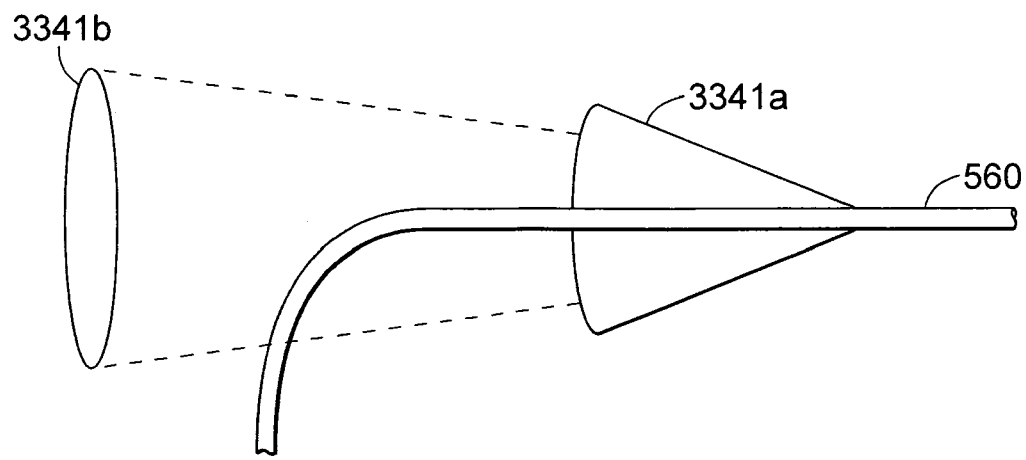
FIG. 33 illustrates a diagrammatical view of various embodiments of a coupling optical element comprising two portions.
Figure 34:
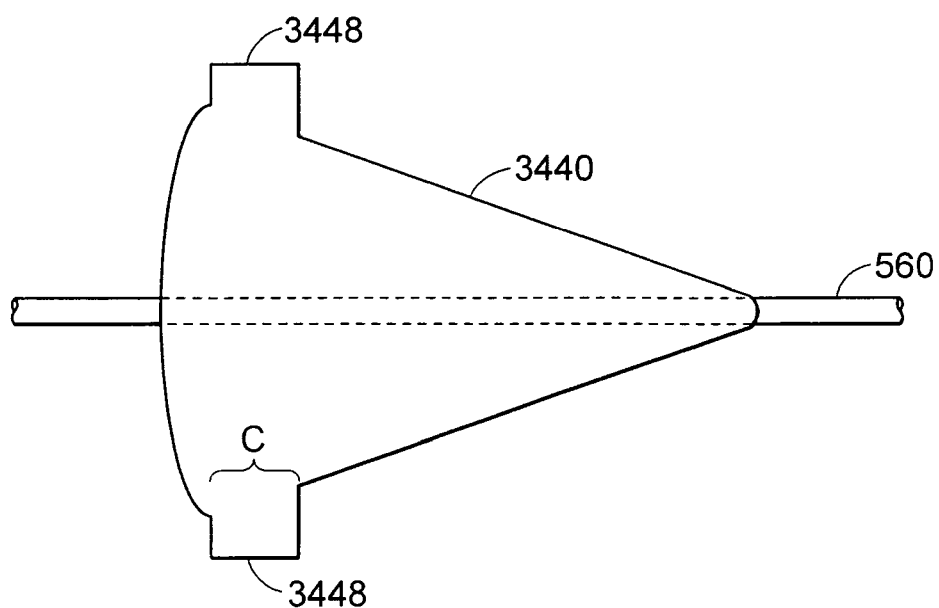
FIG. 34 illustrates a diagrammatical view of various embodiments of a coupling optical element including mounting features.

In various embodiments, first coupling optical element 3140 and/or second coupling optical element 3141 can be formed of a plurality of sections. Examples of a coupling optical element 3240 formed from a plurality of sections joined with an index matching compound or an index matching liquid are shown in FIGS. 32A-C. The various sections are depicted by dotted lines A-A and B-B. In various embodiments, no index matching is used. In various embodiments, second coupling optical element 3141 can be formed by a plurality of spaced apart sections. FIG. 33 shows an example of a second optical element 3141 formed by two spaced apart sections 3341a and 3341b. In various embodiments, section 3341a can be joined to housing 560 as disclosed herein. Section 3321b can be disposed apart from and un-joined to section 3321a and housing 560. First coupling optical element 3140 and/or second coupling optical element 3141 can further include mounting features. Referring to FIG. 34, a coupling optical element 3440 can be coupled to a housing 560 as disclosed herein. Coupling optical element 3440 can also include mounting features 3448 that can be used, for example, to mount or stabilize coupling optical element 3440. In various embodiments, mounting features 3448 can be located within a region C on the surface of coupling optical element 3440 to avoid a loss in efficiency.

Referring again to FIG. 31, excitation light 250 can be directed into first coupling optical element 3140. First coupling optical element 3140 can couple excitation light 250 into housing 560. Excitation light 250 can then interact with the sample within housing 250 at a zone 3065. The interaction can be, for example, light absorbance and/or fluorescent emission. After interacting with the sample, a light 251 can be coupled out of housing 560 by second coupling optical element 3141 and directed towards a detector (not shown).

All publications and patent applications referred to herein are hereby incorporated by reference to the same extent as if each individual publication or patent application was specifically and individually indicated to be incorporated by reference.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a mask" includes two or more different masks. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. A method for exciting fluorescence of samples comprising:
   transporting a plurality of samples through a detection zone with a capillary;
   directing a non-coherent light into the capillary with a coupling optical element and an index matching compound that optically couples the coupling optical element and the capillary;
   wherein said directing a non-coherent light into the capillary with a coupling optical element comprises focusing the non-coherent light onto an end of the capillary with at least one of a truncated sphere and a meniscus lens.

2. A method for exciting fluorescence of samples comprising:
   transporting a plurality of samples through a detection zone with a capillary;
   directing a non-coherent light into the capillary with a coupling optical element and an index matching compound that optically couples the coupling optical element and the capillary; wherein said directing a non-coherent light into the capillary with a coupling optical element comprises focusing the non-coherent light through a wall of the capillary with at least one of a truncated sphere and a conical shaped element.

3. A method for exciting fluorescence of samples comprising:
   transporting a plurality of samples through a detection zone with a capillary;
   directing a non-coherent light into the capillary with a coupling optical element and an index matching compound that optically couples the coupling optical element and the capillary; wherein said directing a non-coherent light into the capillary with a coupling optical element comprises focusing the non-coherent light through a wall of the capillary with an excitation lens comprising a coupling section joined to the capillary and at least one lens portion joined to the coupling section.

4. A method for exciting fluorescence of samples comprising:
   transporting a plurality of samples through a detection zone with a capillary;
   directing a non-coherent light into the capillary with first and second coupling optical elements and an index matching compound that optically couples the coupling optical elements and the capillary; wherein the first coupling optical element directs the non-coherent light to propagate through the detection zone along a first direction and the second coupling optical element directs the non-coherent light to propagate through the detection zone along a second direction.

5. A system for analyzing samples comprising:
   a light source that provides a non-coherent excitation light;
   at least one housing, wherein the housing transports samples and propagates the non-coherent excitation light by total internal reflection;
   a coupling optical element configured to introduce the non-coherent excitation light into the at least one housing through a wall of the at least one housing;
   a index matching compound disposed between the at least one housing and the coupling optical element, and
   at least one NA enhancing optical element to collect an emitted fluorescence, wherein the NA enhancing optical element is constructed of a first material and the housing is constructed of a second material, wherein the first material has a greater index of refraction than the second material.

6. The system of claim 5, wherein the index matching compound has an index of refraction similar to that of the housing.

7. The system of claim 5, wherein the index matching compound has an index of refraction similar to that of the coupling optical element.

8. The system of claim 5, wherein the index matching compound has an index of refraction less than that of the coupling optical element.

9. The system of claim 8, wherein the index of refraction of the index matching compound is in the range from approximately 1.4 to approximately the refractive index of the coupling optical element.

10. The system of claim 5, wherein the NA enhancing optical element is a truncated sphere.

11. The system of claim 10, wherein the truncated sphere comprises;
    a coupling section joined to a potion of the at least one housing;
    a lens section joined to a top of the coupling section; and
    a second lens section joined to a bottom of the coupling section.

12. The system of claim 5, further comprising a plurality of housings.

13. The system of claim 12, further comprising a detector adapted to detect fluorescent light from multiple housings per cycle.

14. The system of claim 12, further comprising a detector adapted to detect fluorescent light from one housing per cycle.

15. A system for exciting fluorescence of samples comprising:
    a capillary configured to transport a plurality of samples through a detection zone;
    a lens assembly comprising at least one of a truncated sphere and a meniscus lens configured to be optically coupled to the capillary by an index matching compound; and
    a light source configured to direct non-coherent light into the coupling optical element whereby the light is focused onto an end of the capillary by the lens assembly.

16. A system for exciting fluorescence of samples comprising:
    a capillary configured to transport a plurality of samples through a detection zone;
    a coupling optical element comprising at least one of a truncated sphere and a conical shaped element configured to be optically coupled to the capillary by an index matching compound; and
    a light source configured to direct non-coherent light into the coupling optical element and whereby the light is focused through a wall of the capillary by the coupling optical element.

17. A system for exciting fluorescence of samples comprising:
    a capillary configured to transport a plurality of samples through a detection zone;
    a coupling optical element comprising an excitation lens further comprising a coupling section joined to the capillary and at least one lens portion joined to the coupling section, the coupling optical element configured to be optically coupled to the capillary by an index matching compound; and a light source configured to direct non-coherent light into the coupling optical element and whereby the light is focused through a wall of the capillary by the excitation lens.

18. A system for exciting fluorescence of samples comprising:
- a capillary configured to transport a plurality of samples through a detection zone;
- a light source configured to direct non-coherent light into a first and second coupling optical element each coupled to the capillary with an index matching compound and by which propagate the light through the detection zone; wherein the first coupling optical element directs the non-coherent light to propagate through the detection zone along a first direction and the second coupling optical element optically directs the non-coherent light to propagate through the detection zone along a second direction.

* * * * *